US009066971B2

(12) United States Patent
Gho et al.

(10) Patent No.: US 9,066,971 B2
(45) Date of Patent: Jun. 30, 2015

(54) METHOD FOR TREATING AND DIAGNOSING CANCER BY USING CELL-DERIVED MICROVESICLES

(75) Inventors: Yong Song Gho, Pohang-si (KR); Oh Youn Kim, Seoul (KR); Su Chul Jang, Gyeongsangbuk-do (KR); Chang Min Yoon, Pohang-si (KR); Yoon Keun Kim, Pohang-si (KR)

(73) Assignee: POSTECH ACADEMY-INDUSTRY FOUNDATION, Gyeongsangbuk-do (KR)

(*) Notice: Subject to any disclaimer, the term of this patent is extended or adjusted under 35 U.S.C. 154(b) by 0 days.

(21) Appl. No.: 13/807,843

(22) PCT Filed: Jun. 30, 2011

(86) PCT No.: PCT/KR2011/004821
§ 371 (c)(1),
(2), (4) Date: Apr. 12, 2013

(87) PCT Pub. No.: WO2012/002760
PCT Pub. Date: Jan. 5, 2012

(65) Prior Publication Data
US 2013/0195765 A1 Aug. 1, 2013

(30) Foreign Application Priority Data

Jul. 1, 2010 (KR) .................. 10-2010-0063637
Jun. 30, 2011 (KR) .................. 10-2011-0065151

(51) Int. Cl.
*A61K 35/74* (2015.01)
*A61K 9/50* (2006.01)
*A61K 47/46* (2006.01)
*A61K 49/00* (2006.01)
*A61K 47/48* (2006.01)
*A61K 31/616* (2006.01)
*A61K 31/704* (2006.01)
*A61K 38/12* (2006.01)
*A61K 38/16* (2006.01)
*A61K 39/00* (2006.01)

(52) U.S. Cl.
CPC .............. *A61K 35/74* (2013.01); *A61K 9/5068* (2013.01); *A61K 47/46* (2013.01); *A61K 49/0017* (2013.01); *A61K 49/0045* (2013.01); *A61K 49/0097* (2013.01); *A61K 47/48776* (2013.01); *A61K 2039/585* (2013.01); *A61K 31/616* (2013.01); *A61K 31/704* (2013.01); *A61K 38/12* (2013.01); *A61K 38/164* (2013.01); *A61K 49/005* (2013.01)

(58) Field of Classification Search
CPC ........................................... A61K 2039/55555
See application file for complete search history.

(56) References Cited

U.S. PATENT DOCUMENTS

2004/0013689 A1    1/2004  Kadurugamuwa et al.
2010/0035234 A1*   2/2010  Donnelly et al. ............... 435/5
2010/0166840 A1    7/2010  Atthachai et al.

FOREIGN PATENT DOCUMENTS

| EP | 2 027 865 A1 | 2/2009 |
|---|---|---|
| JP | 1989-500752 A | 3/1989 |
| JP | 1996-243378 A | 9/1996 |
| JP | 1998-076155 A | 3/1998 |
| JP | 2003-521494 A | 7/2003 |
| JP | 2006-503822 A | 2/2006 |
| KR | 1020100011581 | 2/2010 |
| WO | WO 87/07503 | 12/1987 |
| WO | WO91-12813 | 9/1991 |
| WO | 2007/047501 * | 4/2007 |
| WO | WO2007-132790 A1 | 11/2007 |
| WO | WO 2010/010983 A1 | 1/2010 |

OTHER PUBLICATIONS

Kim et al. Aug. 18, 2009; Structural modifications of outer membrane vesicles to refine them as vaccine delivery vehicles. Biochimica et Biophysica Acta 1788: 2150-2159.*
Martinez et al. 2007; More aspirin for less cancer? JNCI 99(8): 582-583.*
Pascale Jeannin, et al., OMPA Targets Dendritic Cells, Induces Their Maturation . . . , Nature Immunology, vol. 1, No. 6, pp. 502-509, 2000.
Radoslaw Spiewak, et al., In Vitro Study of Pro-Inflammatory and Anti-Tunour . . . , Ann Agric. Environ. Med., vol. 15, pp. 153-161, 2008.
Eun-Young Lee, et al., Gram-Positive Bacteria Produce Membrane Vesicles: . . . , Proteomics, vol. 9, No. 24, pp. 5425-5436, 2009.
K. Chitcholtan, et al; Outer membrane vesicles enhance the carcinogenic . . . ; Carcinogenesis; vol. 29; No. 12; 2008; pp. 2400-2405.
M.R. Gabri, et al; Complete antitumor protection by perioperative immunization . . . ; Clinical Cancer Research; vol. 12; 2006; pp. 7092-7098.
O.Y. Kim, et al; Immunization with *Escherichia coli* outer membrane vesicles . . . ; Journ. Immunology; vol. 190; 2013; pp. 4092-4102.
K. Park, et al; Outer membrane vesicles derived from *Escherichia coli* induce . . . ; PLOS ONE; vol. 5; Issue 6; Jun. 2010; e11334.
C.M. Unal, et al; Bacterial outer membrane vesicles in disease and preventive medicine; Seminars in Immunopathology; 2010.
Supplementary European Search Report dated Feb. 3, 2014.
Office Action dated Mar. 4, 2014.

* cited by examiner

*Primary Examiner* — Karen Cochrane Carlson
(74) *Attorney, Agent, or Firm* — Lucas & Mercanti, LLP

(57) ABSTRACT

Disclosed is a method for the treatment and/or diagnosis of cancer, using bacterial cell-derived microvesicles, which is highly effective in cancer therapy with a significant reduction in side effects. Also, a method is provided for delivering of a drug therapeutic or diagnostic for a disease, using bacterial cell-derived microvesicles loaded with the drug, thereby treating and diagnosing the disease effectively and specifically.

8 Claims, 23 Drawing Sheets

PBS

Mutant MV
(1 µg/ml)

Mutant MV
(2 µg/ml)

*, P < 0.05

METHOD FOR TREATING AND DIAGNOSING CANCER BY USING CELL-DERIVED MICROVESICLES

CROSS-REFERENCE TO RELATED APPLICATIONS

This application is a 371 of PCT/KR2011/004821, filed on Jun. 30, 2011, which claims the benefit of Korean Patent Application Nos. 10-2010-0063637 and 10-2011-0065151, filed on Jul. 1, 2010 and Jun. 30, 2011, respectfully, the contents of each of which are incorporated herein by reference.

TECHNICAL FIELD

The present invention relates to a method for the treatment and/or diagnosis of cancer, using bacterial cell-derived microvesicles. Particularly, the present invention relates to a method for the therapy of cancer, using components of bacterial cell-derived microvesicles.

BACKGROUND ART

In 1813, Vautier reported the apparent cure of cancer in patients who concurrently suffered from gas gangrene caused by the infection of the anaerobic bacterium *Clostridium perfringens*. Since then, extensive studies have been undertaken on the deliberate injection of various bacteria including *Salmonella typhimurium* in addition to *Clostridium*, with the concept of bacteria-mediated cancer therapy. As a cancer grows over a certain size (approximately 1 mm$^3$), it undergoes an undersupply of oxygen from surrounding vessels, with the formation of hypoxia within the cancer tissue. The cancer tissue in a hypoxia state provides an environment in which anaerobic bacteria are readily likely to proliferate while they might attack surrounding cancer cells to necrosis using various toxins and/or through unknown mechanisms. Various attempts have been made to enhance bacteria-mediated cancer therapy. For example, bacteria are transformed to express anticancer proteins, or are used to deliver a plasmid carrying an anticancer protein gene to a cancer tissue. To mitigate the side effects arising from bacterial proliferation and toxins, auxotrophic mutants, spores, and attenuated bacteria have also been tried for cancer therapy. In spite of these efforts, the use of bacteria in cancer therapy always has the risk of bacterial proliferation in normal tissues or organs surrounding the cancer mass.

There are broadly speaking two different types of cell wall in bacteria, called Gram-positive and Gram-negative. Gram-negative bacteria, such as *Escherichia coli, Neisseria meningitidis, Pseudomonas aeruginosa*, and *Shigella flexneri*, are known to spontaneously shed microvesicles from the outer membrane. The Gram-negative bacterial cell-derived shedding microvesicles are known as outer membrane vesicles typically consisting of a lipid bilayer. They are generally spherical with a size of 20~200 nm, and have various biologically active substances, such as lipopolysaccharide (LPS), and outer membrane proteins, lipids and genetic materials (DNA, RNA) which influence the inflammatory responses of host cells. Bacterial cell-derived shedding microvesicles serve as an information carrier which plays a role in the transport of proteins or genetic materials between homogeneous cells and in cell-to-cell signaling, and contributes to the removal of competitive organisms or the survival of bacteria. In addition, the shedding microvesicles deliver toxins to hosts, thus accounting, in part, for the etiology of bacterial diseases. Reports that shedding microvesicles were found in the blood of patients who died of severe sepsis suggest that shedding microvesicles play an important role in the pathology of sepsis, which is characterized by systemic inflammation. This is also supported by the research finding that bacterial cell-derived shedding microvesicles stimulate host cells to secrete inflammatory cytokines and coagulants.

Gram-positive bacteria including *Bacillus subtilis* and *Staphylococcus aureus* produce shedding microvesicles, which was first found by the present inventors. However, there is a need for more information on components or functions of Gram-positive bacterial cell-derived shedding microvesicles.

Microvesicles that spontaneously shed from various bacteria species have been isolated and observed. Typically, shedding microvesicles are isolated from cell cultures by filtration or ultracentrifugation. In addition, it is known that the production of shedding microvesicles can be controlled with an antibiotic such as gentamicin. Particularly, there is a suggestion that shedding microvesicles prepared by treatment with a detergent might be applied as a vaccine against the infection of *N. meningitidis*, a bacterial pathogen. However, the capacity of these production methods is seriously limited.

In spite of the relationship between cancer and bacteria, there have been no reports on the role of bacterial cell-derived shedding microvesicles in the onset and progression of cancer, particularly, on the application of bacterial cell-derived shedding microvesicles to the treatment and/or diagnosis of cancer, thus far.

DISCLOSURE

Technical Problem

Leading to the present invention, intensive and thorough research of the present inventors resulted in the finding that a composition comprising microvesicles derived from bacteria or transformed bacteria can effectively suppress the growth of cancer.

Accordingly, the present invention provides a method for the treatment and/or diagnosis of cancer, using bacterial cell-derived microvesicles, which is highly effective in cancer therapy with a significant reduction in side effects, and a method for the delivery of a drug therapeutic or diagnostic for a disease, using bacterial cell-derived microvesicles loaded with the drug, thereby treating and diagnosing the disease effectively and specifically.

However, the objects to be achieved by the present invention are not limited to the above-mentioned, and it is therefore, as those skilled in the art will appreciate, that other objects could be apparently understood from the following description.

Technical Solution

In accordance with an aspect thereof, the present invention addresses a pharmaceutical composition for the treatment and/or diagnosis of cancer, comprising bacterial cell-derived microvesicles. The bacteria used in the present invention may come from Gram-positive or Gram-negative bacteria, and may be native or genetically transformed. The composition may further comprise a drug that neutralizes the toxicity of the microvesicles, a drug that enhances the anticancer activity, a nanoparticle therapeutic agent loaded with such a drug and/or cell therapeutic agent.

The nanoparticle therapeutic agent is a particle with a size of 10 nm~10 μm, and examples thereof include, but are not limited to, liposomes, dendrimers, polymers, and microvesicles.

In accordance with another aspect thereof, the present invention addresses a method for the treatment and/or diagnosis of cancer, comprising administering the bacterial cell-derived microvesicles to a subject in need thereof. The microvesicles may be administered simultaneously/sequentially together with a drug that neutralizes the toxicity of the microvesicles, a drug that enhances anticancer activity, a nanoparticle therapeutic agent loaded with such a drug and/or cell therapeutic agent.

In accordance with a further aspect thereof, the present invention addresses a method for preparing bacterial cell-derived microvesicles for the treatment and/or diagnosis of cancer. In the preparation method of the present invention, the bacterial cell-derived microvesicles may be microvesicles that are spontaneously shed from bacteria, or artificial microvesicles.

In one embodiment of the present invention, the method for preparing shedding microvesicles for the treatment or diagnosis of cancer comprises the following steps: adding a drug to a suspension of bacteria or transformed bacteria to give a bacterial suspension containing the drug; and isolating shedding microvesicles loaded with the drug from the bacterial suspension.

In another embodiment of the present invention, the method for preparing shedding microvesicles for the treatment or diagnosis of cancer comprises the following steps: isolating shedding microvesicles from a culture of bacteria or transformed bacteria; and incubating a suspension of the isolated microvesicles with a drug. This method may further comprise isolating shedding microvesicles loaded with the drug for the treatment or diagnosis of cancer.

In a further embodiment of the present invention, the method for preparing artificial microvesicles for the treatment or diagnosis of cancer comprises the following steps: mixing a suspension of bacteria or transformed bacteria with a drug to give a bacterial suspension containing the drug; constructing artificial microvesicles using a process selected from the group consisting of extrusion, ultrasonication, disruption, homogenization, freeze-thawing, electroporation, mechanical degradation, and chemical treatment of the bacterial suspension; and isolating the artificial microvesicles.

In a still further embodiment of the present invention, the method for preparing artificial microvesicles for the treatment or diagnosis of cancer comprises the following steps: constructing artificial microvesicles using a process selected from the group consisting of extrusion, ultrasonication, disruption, homogenization, freeze-thawing, electroporation, mechanical degradation, and chemical treatment of suspension of bacteria or transformed bacteria; and isolating the artificial microvesicles; and incubating a suspension of the isolated microvesicles with a drug. This method may further comprise isolating artificial microvesicles loaded with the drug for the treatment or diagnosis of cancer from the bacterial suspension.

The preparation method according to the present invention may further comprise sterilizing the shedding or artificial microvesicles for the treatment or diagnosis of cancer using a process selected from the group consisting of antibiotic treatment, UV exposure, gamma ray exposure, and filtration.

In accordance with a still further aspect thereof, the present invention provides a pharmaceutical composition comprising bacterial cell-derived microvesicles loaded with a drug therapeutic or diagnostic for cancer.

In accordance with still another aspect thereof, the present invention provides a pharmaceutical composition comprising bacterial cell-derived microvesicles loaded with a drug therapeutic or diagnostic for cancer, the bacterial cell being transformed to target cancer cells or tissues.

Also, a yet further aspect of the present invention envisages a method for delivering a drug therapeutic and/or diagnostic for cancer to a cancer cell or cancer tissue, comprising using bacterial cell-derived microvesicles loaded with the drug, the bacterial cell being transformed to target cancer cells or tissues.

Also, yet another aspect of the present invention envisages a method for treating and/or diagnosing cancer, comprising using bacterial cell-derived microvesicles loaded with the drug, the bacterial cell being transformed to target cancer cells or tissues.

In accordance with a yet still further aspect thereof, the present invention provides a composition for delivering a substance therapeutic and/or diagnostic for a disease, comprising bacterial cell-derived microvesicles loaded with the therapeutic and/or diagnostic substance.

In accordance with yet still another aspect thereof, the present invention concerns a method for delivering a drug therapeutic and/or diagnostic for a disease, comprising using bacterial cell-derived microvesicles loaded with the therapeutic and/or diagnostic drug.

In accordance with an additional aspect thereof, the present invention concerns a method for delivering a drug therapeutic and/or diagnostic for a disease to a cell or tissue of interest, comprising using bacterial cell-derived microvesicles loaded with the therapeutic and/or diagnostic drug, the bacterial cell being transformed to target the cell or tissue of interest.

In accordance with a further additional aspect thereof, the present invention concerns a method for treating and/or diagnosing a disease, comprising delivering microvesicles loaded with a drug therapeutic and/or diagnostic for the disease.

In accordance with another additional aspect thereof, the present invention addresses a drug delivery system for the diagnosis and/or treatment of a disease, comprising microvesicles loaded with a drug therapeutic and/or diagnostic for the disease.

In accordance with a still further additional aspect thereof, the present invention addresses a kit for the diagnosis of a disease, comprising bacterial cell-derived microvesicles loaded with a substance diagnostic for the disease.

In accordance with still another additional aspect thereof, the present invention addresses a method for the treatment of cancer, comprising administering bacterial cell-derived vesicles loaded with a protein as an active ingredient. In this method of the present invention, the protein may be derived from Gram-negative or Gram-positive bacteria. In one embodiment of this method, the microvesicles may be loaded with a drug that neutralizes the side effects of components of the microvesicles, a drug that enhances anticancer activity, a nanoparticle therapeutic agent loaded with such a drug, and/or a cell therapeutic agent.

In accordance with a yet further additional aspect thereof, the present invention addresses a method for the treatment of cancer, comprising administering bacterial cell-derived vesicles loaded with a nucleic acid as an active ingredient. In this method of the present invention, the nucleic acid may be derived from Gram-negative or Gram-positive bacteria. In one embodiment of this method, the microvesicles may be loaded with a drug that neutralizes the side effects of the nucleic acid of the microvesicles, a drug that enhances anticancer activity, a nanoparticle therapeutic agent loaded with such a drug, and/or a cell therapeutic agent.

In accordance with yet another additional aspect thereof, the present invention addresses a method for the treatment of cancer, comprising administering bacterial cell-derived vesicles loaded with a lipid as an active ingredient. In this method of the present invention, the lipid may be derived from Gram-negative or Gram-positive bacteria. In one embodiment of this method, the microvesicles may be loaded with a drug that neutralizes the side effects of the lipid of the microvesicles, a drug that enhances anticancer activity, a nanoparticle therapeutic agent loaded with such a drug, and/ or a cell therapeutic agent.

In accordance with a yet still further additional aspect thereof, the present invention addresses a method for the treatment of cancer, comprising administering bacterial celled-derived microvesicles loaded with two or more components selected from a protein, a nucleic acid and a lipid as active ingredients. In one embodiment of this method, the microvesicles may be loaded with a drug that neutralizes the side effects of the components of the microvesicles, a drug that enhances anticancer activity, a nanoparticle therapeutic agent loaded with such a drug, and/or cell therapeutic agent.

In accordance with yet still another additional aspect thereof, the present invention pertains to the use of a nanoparticle therapeutic agent reconstituted with a protein in treating cancer, the protein being a component of bacterial cell-derived microvesicles.

In accordance with an alternative aspect thereof, the present invention addresses the use of a nanoparticle therapeutic agent loaded with a nucleic acid in treating cancer, the nucleic acid being a component of bacterial cell-derived microvesicles.

In accordance with still another alternative aspect thereof, the present invention addresses the use of a nanoparticle therapeutic agent reconstituted with a lipid in treating cancer, the lipid being a component of bacterial cell-derived microvesicles.

In accordance with yet another alternative aspect thereof, the present invention addresses the use of a nanoparticle therapeutic agent loaded or reconstituted with two or more components of bacterial cell-derived microvesicles in treating cancer.

In accordance with a further still alternative aspect thereof, the present invention addresses a method for treating cancer, comprising administering a component of the bacterial cell-derived microvesicles. In one embodiment of the present invention, the component of bacterial cell-derived microvesicles may be administered simultaneously/sequentially together with a drug that neutralizes the toxicity of the component, a drug that enhances anticancer activity, or a nanoparticle therapeutic agent or cell therapeutic agent loaded with such a drug.

The nanoparticle therapeutic agent is a particle with a size of 10 nm~10 μm, and examples thereof include, but are not limited to, liposomes, dendrimers, polymers, and microvesicles.

In one embodiment of the present invention, the proteins, present as one of the components of the bacterial cell-derived microvesicles, include water-soluble proteins, lipid-soluble proteins, or membrane proteins, but are not limited thereto.

In another embodiment of the present invention, the nucleic acids may include DNA and RNA, but are not limited thereto.

Advantageous Effects

The bacterial cell-derived microvesicles in accordance with the present invention can be applied to the treatment or diagnosis of cancer, with a decrease in the side effects of conventional drugs, whereby the agony and inconvenience of the patient in the course of treatment can be reduced.

Conventional anticancer agents act non-specifically on proliferating cells, causing side effects upon exertion of their cytotoxicity on normal cells. In addition, conventional administration methods allow anticancer agents to be delivered to not only cancer cells or tissues, but also non-cancerous organs, thus causing significant side effects. With an increase in the senescent population, cancer in elderly persons is rising as a social problem. Abnormality of immune functions which lose the capacity of controlling the growth of cancer mainly accounts for the onset and progression of cancer, but there are only rare cases in which cancer is treated by enhancing the defense mechanism of effectively suppressing the growth of cancer.

The bacterial cell-derived microvesicles of the present invention can be used in effectively suppressing the grown of cancer. Once they are loaded with a targeting molecule, microvesicles derived from bacterial cells, whether or not transformed, can be directed towards cancer vessels, cells or tissues, thus minimizing the adverse effects resulting from the erroneous targeting of microvesicles. In addition, when a drug such as an anticancer agent, an anti-inflammatory agent, etc., is loaded thereto or encapsulated thereinto, the microvesicles can deliver the drug accurately and thus maximizes the therapeutic effect of the drug, while neither being directed toward off-target cells, nor causing side effects. In addition, microvesicles that are reduced in toxicity and improved in therapeutic capacity can be prepared using a genetic, chemical or mechanical process according to the present invention.

Moreover, the bacterial cell-derived microvesicles of the present invention have the advantage of being used in simultaneously treating and diagnosing cancer. Particularly, microvesicles derived from bacteria that are transformed to target cancer cells or tissues of interest, or bacterial cell-derived microvesicles that display a molecule targeting cancer cells or tissues of interest or that are loaded with an externally detectable substance, such as a fluorescent agent, can be simultaneously applied to the treatment and the diagnosis of cancer.

Further, the bacterial cell-derived microvesicles of the present invention may be applied to the treatment and diagnosis of diseases other than cancer when they loaded with substances pertinent to the treatment and diagnosis of the diseases. The microvesicles can deliver the substances specifically to target cells or tissues, thus improving the treatment and diagnosis of the diseases.

Another advantage of the bacterial cell-derived microvesicles of the present invention have is the mass production thereof, together with the applicability thereof to a wide spectrum of subjects.

Furthermore, so long as it is expressed by bacterial cells, any targeting molecule, therapeutic substance or diagnostic substance may be loaded on or within bacterial cell-derived microvesicles without purification. The loaded substances can perform their inherent functions effectively.

Moreover, the bacterial cell-derived microvesicles with therapeutic and/or diagnostic substances loaded thereto and the preparation method thereof in accordance with the present invention may be used for in vitro and/or in vivo treatment, diagnosis or experiments.

DESCRIPTION OF DRAWINGS

FIG. 14 is a graph showing the effects of microvesicles derived from wild-type *E. coli* (wild-type MV) and mutant *E. coli* transformed to have reduced toxicity of lipopolysaccharides (mutant MV) on the side effect (death caused by systemic inflammation) of *E. coli*-derived shedding microvesicles.

FIG. 17 is a view showing hemolysis observed on a blood agar plate after microvesicles derived from mutant *E. coli* transformed to have reduced toxicity of lipopolysaccharides (mutant *E. coli* MV) are incubated on the plate.

BEST MODE

Figure 1:
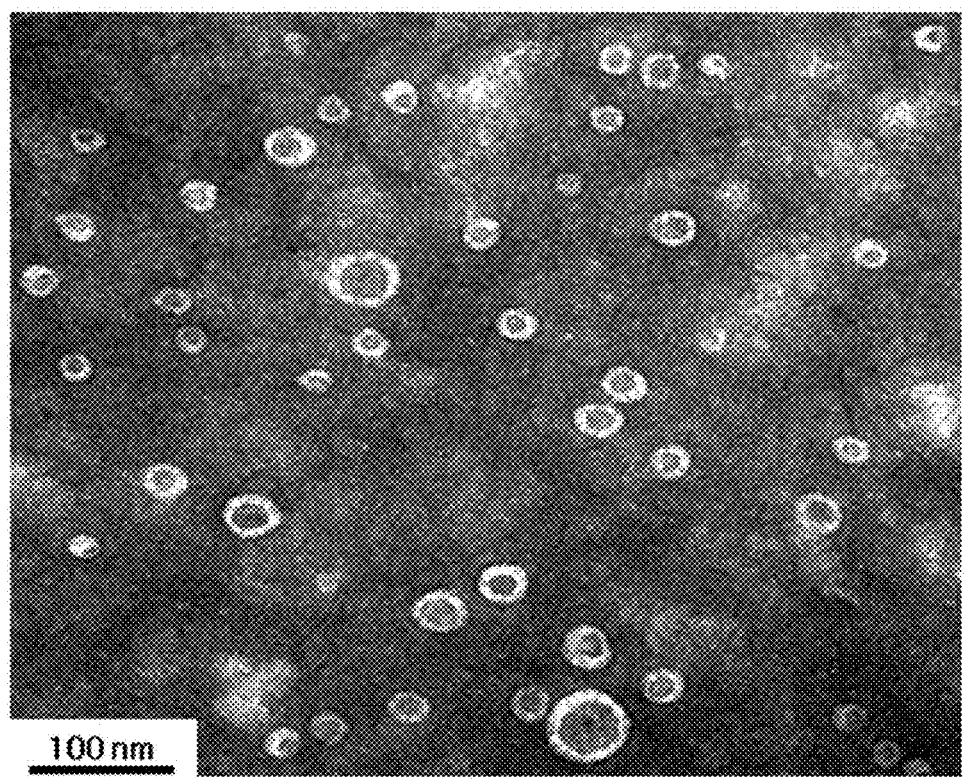
FIG. 1 is a TEM image showing microvesicles constructed from the Gram-negative bacterium *E. coli* by extrusion.

In accordance with an aspect thereof, the present invention provides a pharmaceutical composition for the treatment and/or diagnosis of cancer, comprising bacterial cell-derived microvesicles.

The bacteria useful in the present invention may be Gram-negative or Gram-positive. Exemplary among the Gram-negative bacteria are *E. coli, Pseudonomas aeruginosa*, and *Salmonella* sp. Examples of the Gram positive bacteria include *Staphylococcus aureus* and *Lactobacillus acidophilus*, but are not limited thereto.

As used herein, the term "bacteria" refers to naturally occurring bacteria or transformed bacteria. More specifically, the term "transformed bacteria," as used herein, is intended to include, but is not limited to, bacteria that have been transformed to have reduced toxicity, for example, have a modified endotoxin gene; bacteria that have been transformed to express a substance necessary for targeting cells or tissues of interest, for example cancer vessels, cancer tissues or cancer cells; and bacteria that have been transformed to express a substance necessary for cell membrane fusion with a target cell, therapy and/or diagnosis of a disease of interest; and bacteria that have been transformed to both upregulate a substance of interest and downregulate a substance of interest.

Further, the bacteria may be transformed two or more times by treating the cells with a substance, or by introducing a foreign gene into the cells.

In one embodiment of the present invention, the bacteria may be transformed to downregulate at least one protein of interest.

In one embodiment of the present invention, the transformed bacteria may be adapted to express one or more substances selected from the group consisting of, but not limited to, a cell adhesion molecule, an antibody, a targeting protein, a cell membrane fusion protein, and a fusion protein thereof.

As used herein, the term "bacterial cell-derived microvesicles" is intended to encompass both "shedding microvesicles", which are spontaneously secreted from bacteria, and "artificial microvesicles," which are artificially synthesized using a genetic, chemical or mechanical process.

The term "bacterial cell-derived microvesicles," as used herein, refers to sub-cell sized vesicles, the interior of which is separated from the outside environment only by a lipid bilayer membrane and which have plasma membrane lipids, plasma membrane proteins, nucleic acid, and bacterial components.

The shedding microvesicles of the present invention may be constructed using one of the following illustrative, non-limiting methods.

(1) Culturing bacteria or transformed bacteria, and filtering and ultracentrifuging the culture to give shedding microvesicles.

(2) Treating bacteria or transformed bacteria with a detergent, and filtering and ultracentrifuging the culture to give shedding microvesicles. No limitations are imparted to the detergent.

(3) Treating bacteria or transformed bacteria with an antibiotic, and filtering and ultracentrifuging the culture to give shedding microvesicles. The antibiotic is not imparted with particular limitations, and includes gentamycin, ampicillin, and kanamycin.

The artificial microvesicles of the present invention may be constructed using a method selected from the group consisting of, but not limited to, extrusion, ultrasonication, disruption, homogenization, freeze-thawing, electroporation, mechanical degradation, and chemical treatment of a suspension containing bacteria.

In one embodiment of the present invention, the bacterial cell-derived microvesicles may further comprise components in its membrane other than those derived from the cell membrane of the bacteria.

The components other than those derived from the cell membrane may include targeting molecules, fusogens, which are necessary for membrane fusion with target cells, cyclodextrins, and polyethylene glycol. In addition, the components other than those derived from the cell membrane may be added using a variety of methods, including chemical modification of cell membranes.

For example, membrane components of the bacterial cell-derived microvesicles may be chemically modified with thiol (—SH) or amine (—$NH_2$) groups or by chemically bonding polyethylene glycol to the membrane.

The method for preparing bacterial cell-derived microvesicles according to the present invention may further comprise the chemical modification of membrane components.

According to one embodiment of the present invention, the pharmaceutical composition may further comprise a drug that functions to neutralize the toxicity of the microvesicles themselves. In this regard, the drug may be loaded to the microvesicles. The drug may function to suppress the toxicity of endotoxins, and may be polymyxin B.

According to another embodiment of the present invention, the pharmaceutical composition may further comprise a drug that enhances anticancer activity. In this regard, the drug may be loaded to the microvesicles. The drug useful in the present invention includes a drug suppressive of the immune response of Th17 (T helper 17), a drug suppressive of the production or activity of interleukin 6 (IL-6), a drug suppressive of the production or activity of vascular endothelial growth factor (VEGF), a drug suppressive of STAT3 (signal transducer and activator of transcription 3) signaling, an anticancer agent, a nanoparticle therapeutic agent loaded with such a drug, and a cell therapeutic agent for cancer. The drug suppressive of the immune response of Th17 may be aspirin, and the drug suppressive of the formation or activity of VEGF may function to interrupt with VEGF receptor-mediated signaling. An anticancer agent-loaded nanoparticle may be a liposome such as DOXIL.

The nanoparticle therapeutic agent is a particle with a size of 10 nm~10 μm, and examples thereof include, but are not limited to, liposomes, dendrimers, polymers, and microvesicles.

In addition to the active ingredients, the pharmaceutical composition of the present invention may comprise a pharmaceutically acceptable carrier, for example, saline, sterile water, Ringer's solution, buffered saline, cyclodextrin, a dextrose solution, a maltodextrin solution, glycerol, ethanol, liposome, or a combination thereof. If necessary, the pharmaceutical composition may further comprise a typical additive such as an antioxidant, a buffer, etc. Furthermore, the pharmaceutical composition may be formulated into injections such as aqueous solutions, suspensions, emulsions, etc., pills, capsules, granules or tablets, with the aid of a diluent, a dispersant, a surfactant, a binder and/or a lubricant. Moreover, the pharmaceutical composition may be formulated into suitable dosage forms according to a method that is well known in the art or the method disclosed in Remington's Pharmaceutical Science, Mack Publishing Company, Easton Pa. No particular limitations are imparted to the formulations of the pharmaceutical composition. Preferably, the pharmaceutical composition may be formulated into injections or inhalable forms.

No particular limitations are imparted to the administration of the pharmaceutical composition of the present invention. The pharmaceutical composition may be administered orally or parenterally such as intravenously, subcutaneously, intraperitoneally, via inhalation, or topically. The amount of the active ingredient in the pharmaceutical composition of the present invention may vary depending on various factors including a patient's weight, age, gender and health condition, diet, the time of administration, the route of administration, the rate of excretion, the severity of disease, and the like. The term "daily dose" means an amount of the therapeutically effective ingredient of the present invention which is sufficient to reduce the condition of disease when it is administered to a subject in need thereof. A suitable dose of the active ingredient in the pharmaceutical composition of the present invention may depend on kind of the loaded compounds, disease severity, and the condition of a subject in need of treatment, and can be determined by those skilled in the art. For example, the suitable dose of the composition of the present invention may vary depending on a patient's weight, age, gender and health condition, the route of administration, and the severity of disease, and generally ranges from 0.1 to 1000 mg/day, and preferably from 1 to 500 mg/day, based on adult patients with a weight of 70 kg. The total effective amount of the pharmaceutical composition of the present invention can be administered to patients in a single dose or can be administered by a fractionated treatment protocol, in which multiple doses are administered over a more prolonged period of time.

In accordance with another aspect thereof, the present invention pertains to a method for the treatment and/or diagnosis of cancer, comprising administering the bacterial cell-derived microvesicles to a subject in need thereof.

As used herein, the term "subject" refers to an animal in need of the treatment of a disease of interest (e.g., cancer, vascular diseases or inflammatory diseases), including a human, or non-human mammals such as primates, mice, rats, dogs, cats, horses, cows, etc.

As used herein, the term "cancer" refers to a group of different diseases, which are characterized by unregulated cell growth and infiltration to neighboring tissues due to the disruption of programmed cell death. A target to be treated according to the present invention may be selected from a cancer selected from the group consisting of, but not limited to, carcinoma originating from epithelial cells, such as lung cancer, larynx cancer, stomach cancer, large intestine/rectal cancer, liver cancer, gallbladder cancer, pancreatic cancer, breast cancer, uterine cervical cancer, prostate cancer, kidney cancer, skin cancer, etc., sarcoma originating from connective tissue cells, such as bone cancer, muscle cancer, fat cancer, fibrous cell cancers, etc., blood cancer originating from hematopoietic cells, such as leukemia, lymphoma, multiple myeloma, etc., and neuroma, a tumor of nervous tissues.

As used herein, the term "vascular disease" refers to a group of different diseases in which dysfunction is generated within blood vessels or in vessel walls due to metabolic, infectious, toxic or immune causes. A target to be treated according to the present invention may be selected from a vascular disease selected from the group consisting of, but not limited to, arteriosclerosis (or atherosclerosis), angina pectoris, acute myocardial infarction, stroke, vascular dementia, metabolic vascular diseases, such as ischemic vascular diseases, and infectious, toxic or immune vascular diseases such as sepsis, disseminated intravascular coagulation, thrombotic embolism, vasculitis, nephritis, acute respiratory distress syndrome, emphysema, etc.

The term "inflammation," as used herein, refers to a syndrome or symptom including edema, resulting from an abnormal accumulation of body fluid in tissues, congestion due to vascular dilation, increased heat by pyrogen and vasodilatation, and pain induced by arachionic acid metabolites. Inflammation may be classified as acute, sub-acute, and chronic inflammation according to time, and as infectious, allergic, auto-immune, toxic, metabolic and traumatic inflammatory diseases according to pathophysiological conditions. A target to be treated according to the present invention may be selected from the group consisting of, but not limited to, respiratory inflammatory diseases such as rhinitis, sinusitis, otitis media, rhinopharyngitis, laryngitis, bronchitis, asthma, chronic obstructive pulmonary disease, bronchiectasis, bronchiolitis, pneumonia, pulmonary fibrosis, etc., inflammatory diseases of the digestive system such as stomatitis, esophagitis, gastritis, peptic ulcer, irritable bowel syndrome, ulcerative colitis, cholecystitis, cholangitis, pancreatitis, hepatitis, etc., skin inflammation such as atopic dermatitis, psoriasis, etc., cardiovascular inflammatory diseases such as endocarditis, myocarditis, pericarditis, vasculitis, arteriosclerosis, sepsis, etc., inflammatory diseases of the endocrine system, such as thyroiditis, parathyroiditis, diabetes, etc., inflammatory diseases of the urogenital system such as nephritis, nephropathy, interstitial nephritis, orchitis, oophoritis, endometritis, vaginosis, etc., inflammatory diseases of the musculoskeletal system, such as rheumatoid arthritis, spondylarthritis, osteoarthritis, gout, systemic lupus ethematosus, systemic sclerosis, myopathy, Sjogren's syndrome, Behcet's disease, and antiphospholipid syndrome, and inflammatory diseases of the neuropsychiatric system, such as vascular dementia, Alzheimer's disease, neurodegenerative disease, depressive disorder, schizophrenia, etc.

The bacteria and the bacterial cell-derived microvesicles used in the method of the present invention are as described above.

In one embodiment of the present invention, the method may employ bacterial cell-derived microvesicles loaded with a drug which functions to neutralize the side effects of the microvesicles themselves.

The side effects that the bacterial cell-derived microvesicles themselves retain can be reduced in various manners as follows.

(1) Microvesicles may be prepared from bacteria cells which have been genetically transformed to have reduced toxicity. For example, bacteria transformed to mitigate the toxicity of the lipopolysaccharides that mediate the immune response of host cells (msbB mutant), or the toxicity of lipoteichoic acid (LTA) (LTA mutant), can be used as a source of microvesicles.

(2) A drug suppressive of the toxicity of endotoxins may be employed. This drug may be exemplified by polymyxin B. The drug may be administered in combination with the bacterial cell-derived microvesicles, or loaded to the microvesicles by constructing them from a bacteria culture containing the drug.

(3) The side effects can be reduced by a drug functioning as an anti-inflammatory and/or anti-coagulant agent. The drug may include aspirin. When administered in combination with the bacterial cell-derived microvesicles, aspirin prevents the microvesicle-induced side effects such as inflammatory responses, blood coagulation, etc. Alternatively, microvesicles may be constructed from bacteria that have been cultured in the presence of the drug.

(4) The side effects may be reduced by chemically modifying membrane components of the bacterial cell-derived microvesicles. For example, the membrane components may be chemically modified with thiol or amine groups or by bonding polyethylene glycol to the membrane.

(5) Bacterial infection, which may occur upon the administration of bacterial cell-derived microvesicles, may be prevented by sterilization. For example, the bacterial cell-derived microvesicles are sterilized using UV or gamma radiation or through filtration to kill or remove bacteria.

These examples do not limit methods of reducing the side effects of the bacterial cell-derived microvesicles and may be employed individually or in combination.

In another embodiment of the present invention, microvesicles loaded with a drug that potentiates anticancer activity may be used. This drug may be as described above.

In another embodiment of the prevent invention, the microvesicles may be administered to a subject, in combination with a drug suppressive of side effects of microvesicles and/or a drug potentiating anticancer activity, a nanoparticle therapeutic agent loaded with such a drug, and a cell therapeutic agent.

The nanoparticle therapeutic agent is a particle with a size of 10 nm~10 μm, and examples thereof include, but are not limited to, liposomes, dendrimers, polymers, and microvesicles As used herein, the term "loading" refers to, but not limited to, a process of displaying a substance of interest on the surface of the bacterial cell-derived microvesicles or of encapsulating the substance within the microvesicles.

Also, contemplated in accordance with a further aspect of the present invention is a method for the preparation of bacterial cell-derived microvesicles for cancer therapy and/or diagnosis. In the preparation method of the present invention, the bacterial cell-derived microvesicles include shedding microvesicles, which are spontaneously released from bacteria, or artificial microvesicles.

According to one embodiment thereof, the method for the preparation of shedding microvesicles for cancer therapy or diagnosis comprises: adding a drug to a suspension of bacteria or transformed bacteria to give a bacterial suspension containing the drug; and isolating shedding microvesicles loaded with the drug from the bacterial suspension.

According to another embodiment thereof, the method for the preparation of shedding microvesicles for cancer therapy or diagnosis comprises: isolating shedding microvesicles from a culture of bacteria or transformed bacteria; and incubating a suspension of the isolated microvesicles with a drug. This method may further comprise isolating shedding microvesicles loaded with the drug for cancer therapy or diagnosis.

In one embodiment of the present invention, the method for the preparation of artificial microvesicles for cancer therapy or diagnosis comprises: mixing a suspension of bacteria or transformed bacteria with a drug to give a bacterial suspension containing the drug; constructing artificial microvesicles using a process selected from the group consisting of extrusion, ultrasonication, disruption, homogenization, freeze-thawing, electroporation, mechanical degradation, and chemical treatment of the bacterial suspension; and isolating artificial microvesicles loaded with the drug for cancer therapy or diagnosis from the bacterial suspension.

In another embodiment of the present invention, the method for the preparation of artificial microvesicles for cancer therapy or diagnosis comprises: constructing artificial microvesicles using a process selected from the group consisting of extrusion, ultrasonication, disruption, homogenization, freeze-thawing, electroporation, mechanical degradation, and chemical treatment of a suspension of bacteria or transformed bacteria; isolating the artificial microvesicles; and incubating a suspension of the isolated, artificial microvesicles in the presence of a drug. This method may further comprise isolating the artificial microvesicles loaded with the drug for cancer therapy or diagnosis from the suspension of the artificial microvesicles.

The method for the preparation of shedding or artificial microvesicles for cancer therapy or diagnosis in accordance with the present invention may further comprise sterilizing the shedding or artificial microvesicles using a process selected from the group consisting of antibiotic treatment, UV exposure, gamma ray exposure, and filtration.

The preparation method of the present invention may further comprise isolating sub-cell sized, drug-loaded microvesicles.

This isolating step may be carried out using a process selected from the group consisting of a density gradient, ultracentrifugation, filtration, dialysis and free-flow electrophoresis.

According to another embodiment of the present invention, the preparation method may further comprise removing microvesicles whose membranes are topologically different from those of the bacterial cells of origin. After construction of microvesicles, only those microvesicles that have the same membrane topology as that of the source cells may be selected according to purposes. Using antibodies recognizing cytoplasmic domains of membrane proteins, microvesicles in which the cytoplasmic domains are exposed to the outside can be removed. That is, the microvesicles in which the plasma membrane is turned inside out are removed, and only the microvesicles in which the extracellular domains of membrane proteins are positioned so as to be directed towards the outside remain.

In accordance with a still another aspect thereof, the present invention pertains to a pharmaceutical composition comprising bacterial cell-derived microvesicles loaded with a drug for cancer therapy and/or cancer diagnosis.

In accordance with a still further aspect thereof, the present invention pertains to a pharmaceutical composition comprising bacterial cell-derived microvesicles loaded with a drug for cancer therapy and/or cancer diagnosis, the bacterial cell being transformed to target cancer cells or tissues.

Also, a yet further aspect of the present invention envisages a method for delivering a drug for cancer therapy and/or cancer diagnosis to a cancer cell or cancer tissue, comprising using bacterial cell-derived microvesicles loaded with the drug, the bacterial cell being transformed to target cancer cells or tissues.

In accordance with yet another aspect thereof, the present invention envisages a method for treating and/or diagnosing cancer, comprising using bacterial cell-derived microvesicles loaded with the drug, the bacterial cell being transformed to target cancer cells or tissues.

Also, contemplated In accordance with a still yet further aspect of the present invention is a composition for delivering a substance therapeutic and/or diagnostic for a disease, comprising bacterial cell-derived microvesicles loaded with the therapeutic and/or diagnostic substance.

No particular limitations are imparted to the substance to be loaded to the bacterial cell-derived microvesicles. For example, the substance may be one used for therapy and/or diagnosis, or a protein expressed by the bacteria or transformed bacteria themselves. If necessary, the loading substance may not be native to the cells, but may a foreign material. That is to say, the therapeutic and/or diagnostic substance may be at least one derived from the bacteria or introduced from the outside of the bacterial cells. In addition, the substance may be loaded to the surface of microvesicles using, but not limited to, physical, chemical and/or biological methods.

The bacterial cell-derived microvesicles of the present invention may be loaded with the various therapeutic or diagnostic substances in various manners as follows.

First, microvesicles can be prepared from cells which have already been loaded with a therapeutic or diagnostic substance of interest. For example, when cells are cultured in a medium containing the therapeutic or diagnostic substance of interest, they may contain the substance therein. Alternatively, the substance may be introduced into cells by electroporation.

Also, microvesicles which shed from or which are constructed from the cells containing the substance by ultrasonication, extrusion or mechanical degradation are loaded with the substance.

Next, the substance may be loaded into microvesicles in the course of the construction thereof. For instance, when a bacterial cell suspension containing a substance of interest is extruded through a sub-cell size filter, the microvesicles thus formed are loaded with the substance.

In another alternative, shedding microvesicles or artificial microvesicles may be loaded with a substance of interest after they are constructed or formed. For example, the loading can be achieved by electroporating the substance into already prepared shedding microvesicles or artificial microvesicles.

However, it should be appreciated by those skilled in the art that the loading of a substance of interest into microvesicles is not limited to the above-illustrated methods.

Among the therapeutic and/or diagnostic substances useful in the present invention are anticancer agents, anti-inflammatory agents, angiogenesis inhibitors, peptides, proteins, toxins, nucleic acids, beads, microparticles and nanoparticles, but the present invention is not limited thereto.

Examples of the nucleic acids include DNA, RNA, aptamers, LNA (locked nucleic acid), PNA (peptide nucleic acid), and morpholinos, but are not limited thereto.

Illustrative, non-limiting examples of the nanoparticles include iron oxide, gold, carbon nanotubes, and magnetic beads, but are not limited thereto.

In one embodiment of the present invention, the therapeutic and/or diagnostic substance may be a fluorophore, but is not limited thereto. For example, the fluorophore may be a fluorescent protein or quantum dot (Qdot).

In another embodiment of the present invention, the therapeutic and/or diagnostic substance may be one or more anticancer agents.

The microvesicles of the present invention may be guided to specific cells or tissues. The specific tissues may include, but are not limited to, blood vessels, cancer and inflammatory tissues.

In accordance with still yet another aspect thereof, the present invention concerns a method for delivering a drug therapeutic and/or diagnostic for a disease, a nanoparticle therapeutic agent loaded with the drug, and a cell therapeutic agent, comprising using bacterial cell-derived microvesicles loaded with the therapeutic and/or diagnostic drug.

In accordance with an additional aspect thereof, the present invention concerns a method for delivering a substance therapeutic and/or diagnostic for a disease, a nanoparticle therapeutic agent loaded with a substance therapeutic and/or diagnostic for a disease, and a cell therapeutic agent, comprising using microvesicles loaded with the therapeutic and/or diagnostic substance, said microvesicles being derived from bacteria transformed to target a cell or tissue of interest.

The nanoparticle therapeutic agent is a particle with a size of 10 nm~10 μm, and examples thereof include, but are not limited to, liposomes, dendrimers, polymers, and microvesicles.

A substance therapeutic or diagnostic for a disease, a nanoparticle therapeutic agent loaded with a substance therapeutic and/or diagnostic agent, and a cell therapeutic agent can be delivered with the aid of the microvesicles of the present invention.

In one embodiment of the present invention, two or more different therapeutic or diagnostic substances may be delivered to specific cells or tissues.

For instance, the microvesicles loaded with two or more different therapeutic or diagnostic substances may be used to deliver them to specific cells or tissues.

In another embodiment of the present invention, two or more different microvesicles selected from the group consisting of a microvesicle loaded with one therapeutic or diagnostic substance, a microvesicle loaded with two or more different therapeutic or diagnostic substances, and a combination thereof may be used to deliver the therapeutic or diagnostic substance(s). For example, two or more different microvesicles may be administered simultaneously.

In another embodiment of the present invention, two or more different therapeutic or diagnostic substances may be delivered to specific cells or tissues by administering two or more different microvesicles selected from the group consisting of a microvesicle loaded with one therapeutic or diagnostic substance, a microvesicle loaded with two or more different therapeutic or diagnostic substances, and a combination thereof, sequentially.

According to another embodiment of the present invention, microvesicles loaded with one or more therapeutic or diagnostic substances, and a nanoparticle therapeutic agent loaded with one or more therapeutic and/or diagnostic substances, or a cell therapeutic agent may be administered sequentially.

Also, contemplated in accordance with a further additional aspect of the present invention is a method for treatment and/or diagnosis of a disease, comprising delivering bacterial cell-derived microvesicles loaded with a drug therapeutic or diagnostic for a disease to a target cell or tissue.

In accordance with another additional aspect thereof, the present invention addresses a delivery system of a therapeutic or diagnostic drug, comprising bacterial cell-derived microvesicles loaded with the therapeutic or diagnostic drug.

In accordance with a further additional aspect thereof, the present invention addresses a kit for the diagnosis of a disease, comprising bacterial cell-derived microvesicles loaded with a diagnostic substance. The diagnostic substance may be selected from the group consisting of a primer, a probe, an antisense nucleic acid, and an antibody.

[Delivery of a Substance Using Bacterial Cell-Derived Microvesicles]

In the present invention, microvesicles derived from cells targeting a specific tissue or from transformed cells expressing a targeting protein may be employed. In addition, the microvesicles may be derived from transformed cells expressing a fusogen.

It is known that the blood cells, that is, monocytes, lymphocytes, neutrophils, eosinophils, basophils, and platelets, myeloid-derived suppressor cells, and stem cells found in bone marrow, blood, and adipose tissues are guided to cancerous and inflammatory tissues. Hence, microvesicles derived from the membrane of the immune/inflammatory cells or the stem cells are introduced into cancerous and inflammatory tissues. Further, microvesicles derived from bacteria which are transformed to express a protein binding selectively to a substrate expressed on a specific cell or tissue can be guided to the specific cell or tissue. In the present invention, after being loaded with therapeutic or diagnostic substances, microvesicles constructed from such bacterial cells can be used to deliver the substances to target cells, tissues or blood.

There are a variety of plasma membrane proteins that are involved in the guidance of immune/inflammatory cells and stem cells to specific tissues. For example, cell adhesion molecules including integrins such as LFA-1 (leukocyte function-associated antigen-1) and Mac-1 (macrophage-1 antigen) are present on the surface of monocytes. These cell adhesion molecules can bind to other cell adhesion molecules, such as ICAM-1 (intercellular adhesion molecule-1) and VCAM-1 (vascular cell adhesion molecule-1), on vascular cells. Interaction between LFA-1 and ICAM-1 allows monocytes to pass through vascular endothelial cells so that the monocytes can be guided to inflammatory or cancerous tissues.

When transformed to express plasma membrane proteins specific for cancer or tissues of interest on the surface of bacterial cell-derived microvesicles, the microvesicles can be guided to specific tissues, such as vascular tissues, cancerous or tumorous tissues, etc. By way of example, ERBB2 is overexpressed on the surface of breast cancer cells. Microvesicles derived from bacteria which have been transformed to express a fusion protein composed of a bacterial transmembrane protein and an antibody specific for the membrane protein ERBB2 can be allowed to target breast cancer tissues. Further, bacterial cell-derived microvesicles can be guided toward large intestine cancer, pancreatic cancer and lung cancer tissue if they are transformed to express a fusion protein in which an antibody recognizing a carcinoembryonic antigen (CEA) abundantly found in the cancer tissues is fused to a bacterial transmembrane protein.

Bacterial cell-derived microvesicles retain almost the same membrane components as those of the bacterial cells of origin, so that they can be directed toward specific tissues or cells that the bacteria target. If necessary, a nuclease may be employed during the construction of microvesicles to remove nucleic acids unnecessary for the delivery of a therapeutic or diagnostic substance from the microvesicles.

[Bacterial Cell-Derived Microvesicles and Preparation Thereof]

Bacterial cell-derived microvesicles can be readily loaded with various therapeutic or diagnostic substances to be delivered. Hence, microvesicles may be used for mono- or combined therapy or diagnosis or both of therapy and diagnosis (theragnosis, pharmacodiagnosis). In this context, the substances to be delivered may be present inside the microvesicles when encapsulated, within the lipid bilayer when at least partially buried or embedded therein like a transmembrane protein, or on the surface of the microvesicles.

From bacterial cells, microvesicles can be artificially constructed in various sizes like liposomes. Thanks to the EPR (Enhanced Permeability and Retention) effect, generally, molecules with a size of 100 nm or greater may accumulate in cancer tissue for a longer period of time than they do in normal tissues. Accordingly, a drug loaded to microvesicles with a size of 100 nm or greater is advantageous in diagnosis and therapy because it can stay much longer in cancer tissue, thereby enhancing a therapeutic or diagnostic effect. On the other hand, when inhaled, only particles with a size of 1 μm or smaller are allowed to reach the alveoli due to the pulmonary structure. A substance, for example, an inflammation inhibitor for the treatment of asthma, can be delivered to lung tissue if it is loaded to microvesicles which are smaller than 1 μm in size. As described, various sizes of microvesicles may be constructed depending on the tissue to which the loaded substance is to be applied. Preferably, the microvesicles of the present invention range in size from 10 nm to 10 μm.

When a therapeutic and/or diagnostic substance loaded to the microvesicles of the present invention is administered to a "subject," an immunosuppressant may be used together therewith.

In the present invention, microvesicles may be constructed from all kinds of bacterial cells, for example, bacteria that can be directed to a target, such as specific cells or tissues, by transformation. For use in the delivery of a substance to a specific tissue, microvesicles may be constructed from bacterial cells which are directed toward the specific tissue. Also, when constructed from cells in which proteins directed toward specific tissues are upregulated and/or proteins involved in non-specific guidance are downregulated, microvesicles can be effectively used to deliver a therapeutic or diagnostic substance to, for example, blood vessels, cancer tissues, or inflammatory tissues.

The transformation of bacterial cells can be achieved using typical methods known in the art, for example, by stimulating the cells or introducing a foreign gene into the bacterial cells to modify, e.g., upregulate or downregulate, the expression of proteins of interest. A specific stimulus may induce a change in the expression of a protein of interest. The introduction of a foreign gene may induce the expression or inhibition of a protein of interest. In this context, plasmid DNA, RNA or a phage is introduced into cells using electroporation, microinjection, ultrasound mediation or other methods known in the art.

After bacteria are transformed to express a protein or an antibody capable of binding to cancer cells, tissues or vessels or inflammatory tissues, solely or as a fusion protein on the surface thereof, microvesicles can be constructed from the bacterial cells. In addition, microvesicles may be prepared from bacterial cells expressing a therapeutic and/or diagnostic substance or bacterial cells transformed to express a therapeutic and/or diagnostic substance. Moreover, microvesicles may be prepared from bacterial cells expressing a combination of the above substances or bacterial cells transformed to a combination of the above substances. To suppress the expression of specific protein, antisense RNA, LNA, PNA, and the like can be used. When microvesicles constructed from bacterial cells are directed toward two targets, the bacterial cells may be transformed in such a way that the expression of one or more specific proteins is inhibited to reduce the guidance of the cells to one of the two targets. Hence, the specificity in the delivery of the substance for microvesicles derived from the transformed cells is enhanced. Alternatively, bacterial cells which have undergone two or more rounds of transformation may be used. For example, primary transformants may be subjected to secondary transformation before being used as a source for constructing microvesicles. However, the preparation method of the present invention is not limited to those mentioned above.

The microvesicles according to the present invention may be constructed using various mechanical, electrical or chemical methods. Among the methods are cytolysis using osmosis, electroporation, sonication, homogenization, detergent treatment, freeze-thawing, extrusion, mechanical degradation, and chemical treatment, but these methods do not limit the present invention. In a mechanical degradation method, a solution of cells is shaken together with a metal, ceramic or sufficiently hard plastic balls. In the context of extrusion, cells are forced to sequentially pass through filters starting with large pores and going down to smaller pores. For example, cells are sequentially passed through three filters with respective pore sizes of 10 μm→5 μm→1 μm to form microvesicles.

[Therapeutic or Diagnostic Substance]

The substance useful in the present invention may include, but is not limited to, a substance that bacteria or transformed bacteria express or a foreign substance that the bacteria do not express.

For use in the present invention, a therapeutic or diagnostic substance may be loaded to microvesicles or may be administered in combination with microvesicles according to needs and purposes.

In one embodiment of the present invention, the therapeutic or diagnostic substance may be administered as it is or as a complex with a nanoparticle therapeutic agent or cell therapeutic agent, in combination with microvesicles.

The nanoparticle therapeutic agent is a particle with a size of 10 nm~10 μm, and examples thereof include, but are not limited to, liposomes, dendrimers, polymers, and microvesicles.

As therapeutic or diagnostic substances which can be loaded to the microvesicles of the present invention or to the nanoparticle or cell therapeutic agent, various materials including proteins or peptides, nucleic acids, lipids and metabolites, all being derived from nucleated, mammalian cells, may be used without limitation.

Examples of the loadable proteins or peptides useful in the present invention include, but are not limited to, growth factors, such as VEGF, EGF (epidermal growth factor), etc., cytokines such as IL-1, IFN-γ (interferon-gamma), IL-10, etc., antibodies, receptors, and fluorescent proteins. The proteins or peptides may be expressed within cells or displayed on plasma membranes. Also, their entirety or active sites may be expressed solely or as fusion proteins. It is known that the activity of proteins or peptides displayed on microvesicles is higher than when they exist solely within cells as a result of the higher local concentration. Proteins or peptides on microvesicles may act as ligands to trigger signaling or as antagonists to inhibit the function of various ligands.

Examples of the nucleic acids loadable to the microvesicles or the nanoparticle or cell therapeutic agent according to the present invention include DNA, miRNA (microRNA), siRNA (small inferring RNA), antisense RNA, and sense RNA, but are not limited thereto. These nucleic acids may be used to evoke sense effects, antisense effects, RNA interference, or inhibition of protein functions.

As the foreign therapeutic or diagnostic substance loadable to the microvesicles or the nanoparticle or cell therapeutic agent, anticancer agents, anti-inflammatory agents, angiogenesis inhibitors, peptides, proteins, toxins, nucleic acids, beads, microparticles and nanoparticles may be used without limitation.

An anticancer agent is a generic term of a drug used to suppress the growth and metastasis of cancer. Most anticancer agents act to block the replication, transcription and/or translation of cancer cells. No particular limitations are imparted on kinds of the anticancer agents useful in the present invention. Under the general principle in which kinds of cancer cells, absorption rates of anticancer agents (the duration of treatment, the route of administration, etc.), positions of tumor, sizes of tumor, etc. are taken into consideration, anticancer agents may be selected. Examples of the anticancer agents useful in the present invention include DNA alkylating agents, such as mechlorethamine, chlorambucil, phenylalanine, mustard, cyclophosphamide, ifosfamide, carmustine (BCNU), lomustine (CCNU), streptozotocin, busulfan, thiotepa, cisplatin and carboplatin, anti-cancer antibiotics, such as dactinomycin (actinomycin D), doxorubicin (adriamycin), epirubicin, idarubicin, mitoxantrone, plicamycin, mitomycin and C Bleomycin, and plant alkaloids, such as vincristine, vinblastine, paclitaxel, docetaxel, daunorubicin, taxol, oncovin, prednisone, cisplatin, herceptin, rituximab, etoposide, teniposide, topotecan and iridotecan. Also, radioactive substances known in the art may be used. However, the anticancer agents useful in the present invention are not limited to the examples.

Further, the anti-inflammatory agent loadable to the microvesicles or the nanoparticle or cell therapeutic agent of the present invention is selected from the group consisting of, but not limited to, dexamethasone, indomethacin, ibuprofen, clobetasol propionate, diflorasone diacetate, halobetasol propionate, amcinonide, fluocinonide, mometasone furoate, desoximetasone, diclofenac and piroxicam.

As used herein, the term "angiogenesis inhibitor" refers to a drug that functions to suppress the growth of new blood vessels from preexisting vessels. Most angiogenesis inhibitors have the function of suppressing the growth and metastasis of cancer, and inflammatory reactions. No particular limitations are imparted to the kinds of the angiogenesis inhibitors available as the therapeutic substance of the present invention.

The therapeutic or diagnostic substance loaded to the microvesicles or the nanoparticle or cell therapeutic agent according to the present invention may include proteins or peptides. For example, RNase A, growth factors, such as VEGF and EGF, cytokines, such as IL-1, IFN-gamma and IL-10, antibody therapeutics, DNase, and various proteins or peptides suppressing the growth and metastasis of cancer cells and inflammatory responses may be employed without limitations.

Also, the therapeutic or diagnostic substance loaded to the microvesicles or the nanoparticle or cell therapeutic agent according to the present invention may include toxins. The term "toxin" refers to a poisonous substance produced within living cells or organisms, which is capable of causing a disease on contact with or adsorption by body tissues. Using a toxin, cell death can be induced. No particular limitations are imparted to the kind of toxin available as the therapeutic substance of the present invention.

Representative among the nucleic acids loadable to the microvesicles or the nanoparticle or cell therapeutic agent according to the present invention are DNA, miRNA, siRNA, antisense RNA, sense RNA, and aptamers. Also, nucleic acid analogs such as LNA, PNA, and morpholinos may be loaded to the microvesicles or the nanoparticle or cell therapeutic agent, but not limited thereto. These nucleic acids may be used to evoke sense effects, antisense effects, RNA interference, or inhibition of protein functions.

In the present invention, microvesicles loaded with nucleic acids encoding fluorescent proteins or with various fluorescents can be used for diagnosis. When microvesicles designed to target specific cells or tissues are loaded with a plasmid DNA carrying a gene encoding a fluorescent protein and introduced into the body, the fluorescence signal emitted from the fluorescent protein makes it possible to recognize where the target cells or tissues exist. Likewise, fluorescent quantum dots or other various fluorescents may be loaded to microvesicles and used to detect the position of specific cells and tissues within the body. That is, fluorescence generated from target cells or tissues can be used for diagnosis. In addition, fluorescence-emitting quantum dots may be applied to the treatment of diseases because they induce apoptosis.

Therapeutic or diagnostic substances other than fluorescents, loadable to the microvesicles, may be exemplified by microparticles or nanoparticles. Examples include iron oxide particles, gold particles and carbon nanotubes, but are not limited thereto. Magnetic beads may be used as the therapeutic or diagnostic substance and loaded into the microvesicles. Magnetic particles such as iron oxide may be used as an image contrasting agent for MRI (magnetic resonance imaging). Moreover, nucleic acids or proteins conjugated with nanoparticles may be employed. Diagnostic radioactive substances are also available.

Two or more different substances can be delivered by the microvesicles of the present invention. For example, the microvesicles with two or more different substances simultaneously loaded thereto may be used to deliver the substances. Alternatively, microvesicles loaded with different substances individually or in combination are employed in combination so that two or more different substances can be delivered. In order to deliver three different substances, for instance, a first, a second and a third microvesicle may be loaded with the three different substances, respectively. On the other hand, a fourth microvesicle with two different substances simultaneously loaded thereto and a fifth microvesicle with another different substance loaded thereto may be used to deliver the three different substances. The first, the second and the third microvesicles may be used simultaneously or sequentially. Likewise, the fourth and the fifth microvesicles may be used simultaneously or sequentially.

There are various methods for isolating microvesicles from other molecules or other cellular components, examples of which include a density gradient, ultracentrifugation, filtration, dialysis, and free flow electrophoresis, but these are not limited thereto.

A density gradient process, one of the most popular processes for distinguishing materials with different densities, can be applied to the isolation of the microvesicles of the present invention because their densities are different from those of free molecules. For use in the density gradient process, a medium may be selected from among, but not limited to, Ficoll, glycerol, sucrose and OptiPrep™. Microvesicles loaded with or without therapeutic or diagnostic substances may be separated from each other when taking advantage of differences in density therebetween. A density gradient process may be used in combination with centrifugation or electrophoresis. Microvesicles can also be isolated by gel filtration or ultrafiltration. Instead of filtration, dialysis may be adopted to remove small molecules. In addition, free flow electrophoresis is useful for isolating microvesicles of the present invention.

According to purpose, microvesicles within a certain size range may be selected before use. The selection of microvesicles within a certain size range may be carried out before, simultaneously or after loading therapeutic or diagnostic substances thereinto.

In the present invention, microvesicles in which a part of membrane components have been modified may be constructed. For example, when microvesicles are constructed from a mixture of a fusion protein and cells, the fusion protein may be at least partially exposed on the microvesicles. Microvesicles may be converted into stealth-microvesicles by coating with polyethylene glycol. The addition of cyclodextrin to microvesicles may reduce the non-specific targeting of the microvesicles. Exhibiting both hydrophilicity and hydrophobicity, cyclodextrin, when attached onto the surface of microvesicles, can act to block non-specific binding between lipids. The microvesicles or shedding microvesicles may be chemically modified. For example, after microvesicles are constructed from cells whose membrane or transmembrane proteins are at least in part exposed to the outside, various molecules may be chemically bound to the thiol group of cystein residues on the exposed region of the protein. Additionally, membrane components of the microvesicles can be modified by chemical biding of various molecules to the amine group within a membrane protein.

In accordance with an alternative aspect thereof, the present invention provides a method for the treatment of cancer, comprising administering components of bacterial cell-derived microvesicles to a subject in need thereof.

The bacteria useful in the present invention may be Gram-negative or Gram-positive. Exemplary among the Gram-negative bacteria are *E. coli, Pseudonomas aeruginosa*, and *Salmonella* sp. Examples of the Gram positive bacteria include *Staphylococcus aureus* and *Lactobacillus aciophilus*, but are not limited thereto.

Examples of the components of the microvesicles include proteins, nucleic acids, and lipids, but are not limited thereto.

In one embodiment of the present invention, the proteins, present as one of the components of the bacterial cell-derived microvesicles, include water-soluble proteins, lipid-soluble proteins, or membrane proteins, but are not limited thereto.

In another embodiment of the present invention, the membrane proteins may include OmpA, OmpF, OmpC, and flagellin, but are not limited thereto.

In another embodiment of the present invention, the nucleic acids may include DNA and RNA, but are not limited thereto.

In another embodiment of the present invention, the proteins may be associated with at least one selected from the group consisting of, but not limited to, a cell adhesion molecule, an antibody, a targeting protein, a cell membrane fusion protein, and a fusion protein thereof.

In accordance with another alternative aspect thereof, the present invention addresses the use of a nanoparticle therapeutic agent reconstituted with a protein in treating cancer, the protein being a component of bacterial cell-derived microvesicles.

In accordance with a further alternative aspect thereof, the present invention addresses the use of a nanoparticle therapeutic agent loaded with a nucleic acid in treating cancer, the nucleic acid being a component of bacterial cell-derived microvesicles.

In accordance with still another alternative aspect thereof, the present invention addresses the use of a nanoparticle therapeutic agent reconstituted with a lipid in treating cancer, the lipid being a component of bacterial cell-derived microvesicles.

In accordance with yet another alternative aspect thereof, the present invention addresses the use of a nanoparticle therapeutic agent loaded or reconstituted with two or more components of bacterial cell-derived microvesicles in treating cancer.

The nanoparticle therapeutic agent is a particle with a size of 10 nm~10 μm, and examples thereof include, but are not limited to, liposomes, dendrimers, polymers, and microvesicles.

In one embodiment of the present invention, a new substance may be further taken as a component of the bacterial cell-derived microvesicles.

This new substance may include cyclodextrin, and polyethylene glycol. In addition, the new substance can be employed as a component using various methods including chemical modification.

In another embodiment of the present invention, the nanoparticle therapeutic may further comprise a drug that reduces side effects of the component, or a drug that enhances anticancer activity. The drug reducing side effects of the components may be aspirin. The drug enhancing anticancer activity includes a drug suppressive of the immune response of Th17 (T helper 17), a drug suppressive of the production or activity of interleukin 6 (IL-6), a drug suppressive of the production or activity of VEGF (vascular endothelial growth factor), a drug suppressive of STAT3 (signal transducer and activator of transcription 3) signaling, and an anticancer agent. The drug suppressive of the immune response of Th17 may be aspirin, and the drug suppressive of the production or activity of VEGF may function to interrupt with VEGF receptor-mediated signaling.

In one embodiment of the present invention, the component of microvesicles may be administered simultaneously/sequentially together with a drug that neutralizes the toxicity of the component, a drug that enhances anticancer activity, or a nanoparticle therapeutic agent or cell therapeutic agent loaded with such a drug.

The nanoparticle therapeutic agent is a particle with a size of 10 nm~10 μm, and examples thereof include, but are not limited to, liposomes, dendrimers, polymers, and microvesicles.

According to another embodiment of the present invention, two or more different components selected from the group consisting of one component of the microvesicles, two or more different components of the microvesicles, and a combination thereof are administered simultaneously.

According to another embodiment of the present invention, two or more different components selected from the group consisting of one component of the microvesicles, two or more different components of the microvesicles, and a combination thereof are administered sequentially.

According to another embodiment of the present invention, two or more different components selected from the group consisting of one component of the microvesicles, two or more different components of the microvesicles, and a combination thereof are administered in combination with a drug reducing side effects of the components, a drug enhancing anticancer activity, a drug-loaded nanoparticle therapeutic agent, or a cell therapeutic agent, sequentially.

A better understanding of the present invention may be obtained through the following examples which are set forth to illustrate, but are not to be construed as limiting the present invention.

EXAMPLES

Example 1

Construction of Artificial Microvesicles Derived from Gram-Negative Bacteria by Extrusion and Properties Thereof Artificial microvesicles were constructed from Gram-negative bacteria by extrusion.

In this experiment, the Gram-negative bacterium *E. coli* was employed. *E. coli* was cultured to an optical density of 1.0 (at 600 nm) in 50 mL of LB broth. The bacteria cells were collected as a pellet after centrifugation at 3,500×g for 10 min, and the cell pellet was resuspended in PBS (phosphate buffered saline).

This cell suspension was passed three times through each of membrane filters with a pore size of 10 μm, 5 μm, and 1 μm, in that order. In a 5 mL ultracentrifuge tube, 1 mL of 50% OptiPrep, 1 mL of 5% OptiPrep, and 3 mL of the cell suspension effluent from the membrane filters were sequentially placed. Ultracentrifugation at 100,000×g for 3 hrs formed a layer of microvesicles between 50% OptiPrep and 5% OptiPrep.

The artificial microvesicles constructed from the Gram-negative bacterium were analyzed for properties. The Gram-negative bacterial cell-derived, artificial microvesicles were adsorbed for 3 min to a glow-discharged carbon-coated copper grid. The grid was washed with distilled water, and stained for 1 min with 2% uranylacetate before observation under a JEM101 electron microscope (Jeol, Japan). The result is shown in FIG. 1. As can be seen in the transmission electron microscope images of FIG. 1, the microvesicles artificially constructed from bacterial cells by extrusion consisted of a lipid bilayer, and were generally spherical with a size of 10-100 nm.

Example 2

In Vivo Anticancer Activity of Gram-Negative Bacterial Cell-Derived Shedding Microvesicles For use in this experiment, microvesicles that were spontaneously shed from Gram-negative bacteria were isolated. The Gram-negative bacteria *E. coli, Pseudonomas aeruginosa*, and *Salmonella enteritidis* were used as sources of microvesicles. Bacteria were inoculated into 100 mL of LB in an Erlenmeyer flask and cultured at 37° C. for 6 hrs. Of the culture, 8 mL was transferred into 600 mL of LB broth in a 2 L Erlenmeyer flask and cultured at 37° C. for 5 hrs to an optical density of 1.5 (at 600 nm). The resulting culture was divided into 500 mL high speed centrifuge tubes before centrifugation at 10,000×g and 4° C. for 20 min. The supernatant was forced to pass once through a membrane filter with a pore size of 0.45 μm, and then concentrated 25-fold using a Quixstand system equipped with a membrane having a molecular weight cut-off of 100 kDa. The concentrate was passed once through a membrane filter with a pore size of 0.22 μm, and divided into 70 mL ultracentrifuge tubes, followed by ultracentrifugation at 150,000×g and 4° C. for 3 hrs to afford bacteria cell-derived shedding microvesicles as a precipitate. This was suspended in PBS.

The shedding microvesicles derived from *E. coli, P. aeruginosa*, and *S. enteritidis* were assayed for anticancer activity. A mouse colon 26 cell line was subcutaneously injected at a dose of $1 \times 10^6$ cells into mice, and cultured. After one week, a PBS solution containing 1 μg, or 5 μg of each of the Gram-negative bacterial cell-derived microvesicles was injected at a dose of 100 μl twice a week via the tail vein into the mice which were divided into groups, each consisting of three. On day 23 after the transplantation of cancer cells, the sizes of colon cancer tissue were monitored. The volume of cancer tissue was calculated by the equation $V = l \times s^2 / 2$, wherein l is a length of the longest axis of a tumor and s is a length of the axis perpendicular to the longest axis.

Figure 2:
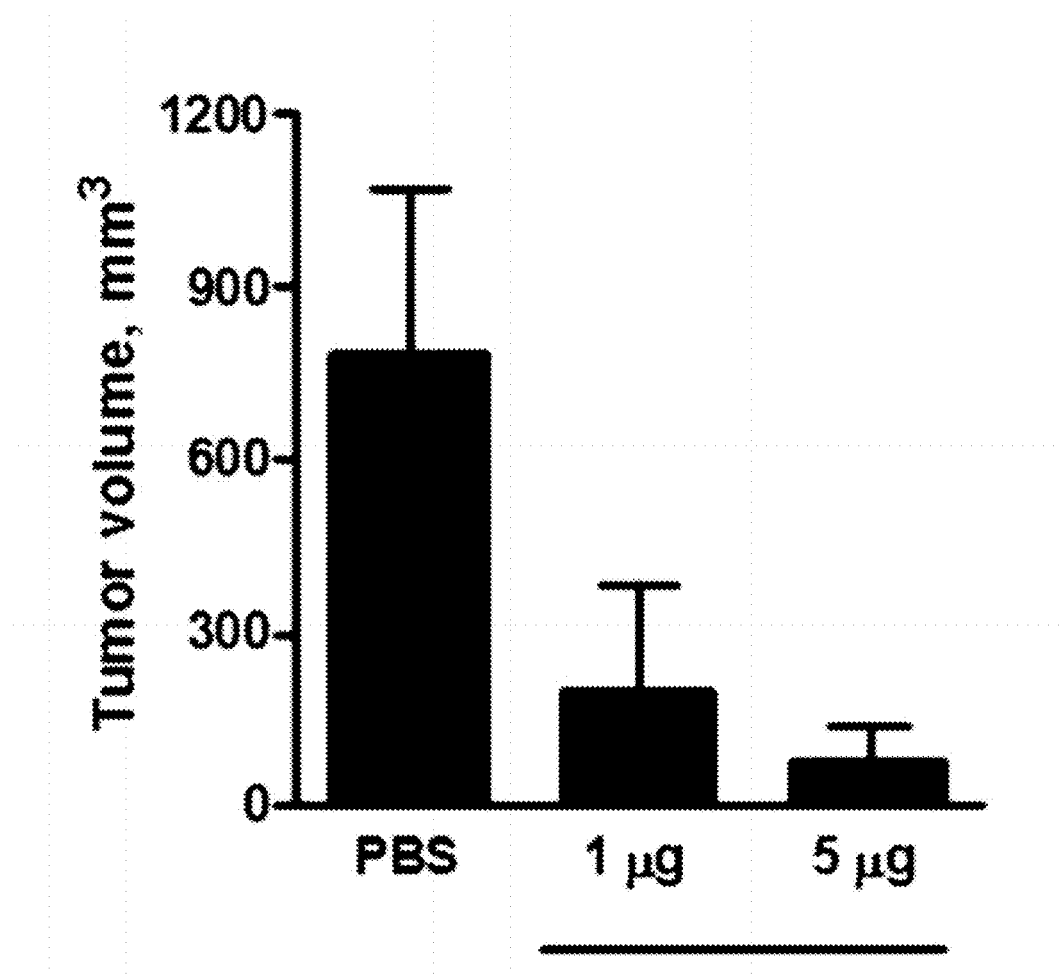
FIG. 2 is a graph showing the inhibition of shedding microvesicles derived from Gram-negative bacterium *E. coli* (E. coli MV) against the growth of cancer tissues (tumor volume) in animal models of colon cancer.
Figure 3:
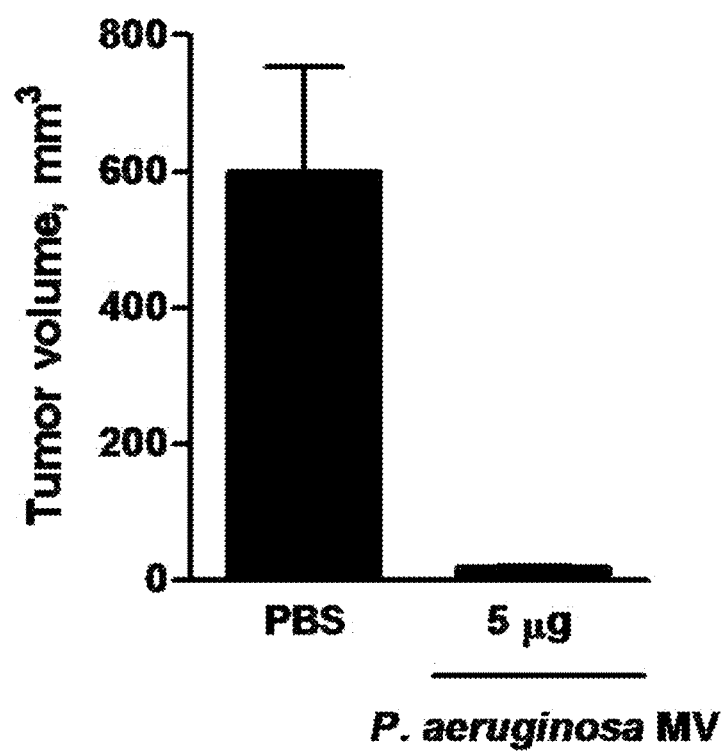
FIG. 3 is a graph showing the inhibition of shedding microvesicles derived from Gram-negative bacterium *P. aeruginosa* (P. aeruginosa MV) against the growth of cancer tissues (tumor volume) in animal models of colon cancer.
Figure 4:
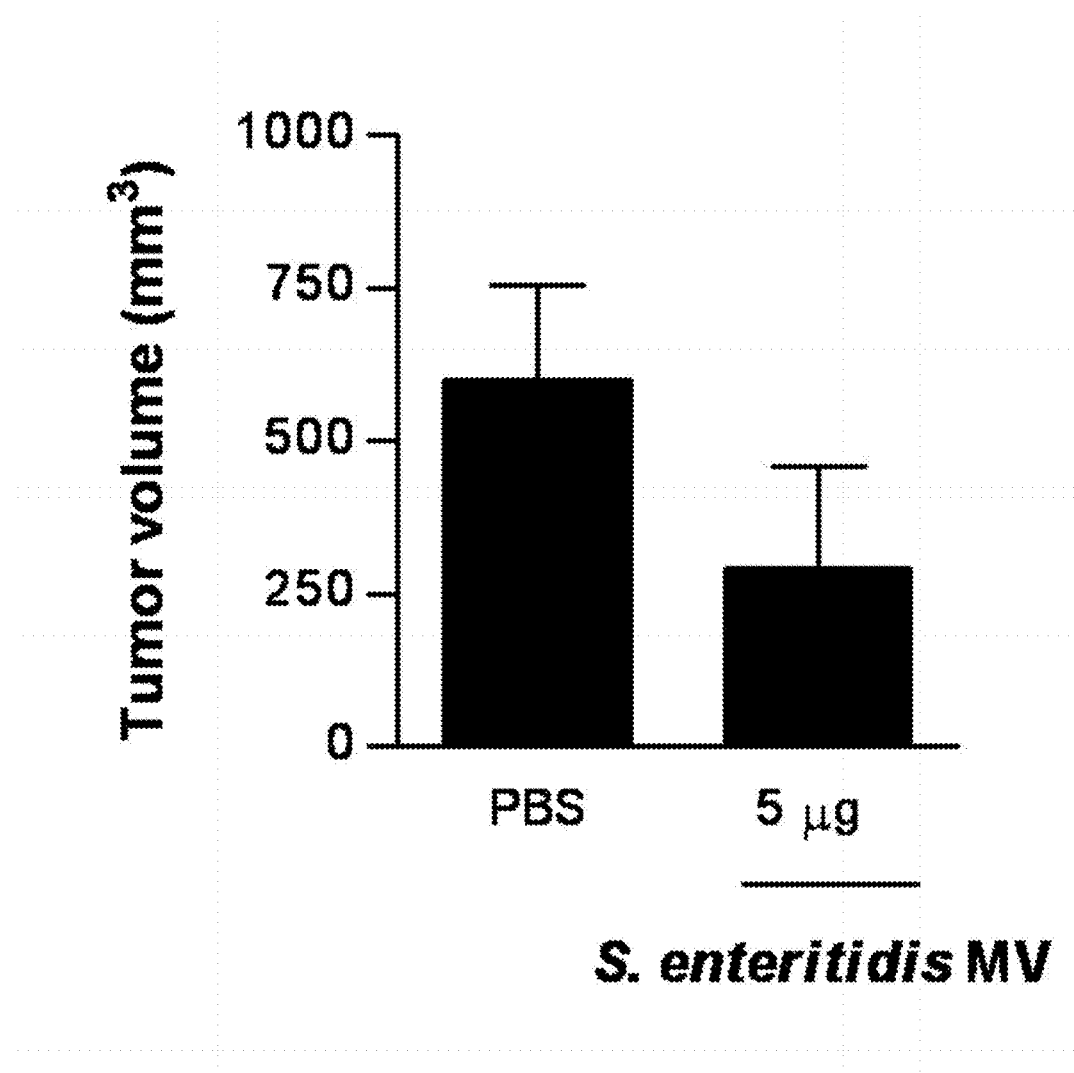
FIG. 4 is a graph showing the inhibition of shedding microvesicles derived from Gram-negative bacterium *S. enteritidis* (S. enteritidis MV) against the growth of cancer tissues (tumor volume) in animal models of colon cancer.

After the subcutaneous transplantation, the volume measurements of colon cancer tissues were as shown in FIGS. 2 to 4. The administration of shedding microvesicles derived from *E. coli* reduced the size of the colon cancer tissue in a dose-dependent manner, compared to the control PBS (FIG. 2). A significant reduction in the size of colon cancer tissues was obtained after shedding microvesicles derived from *P. aeruginosa* were administered (FIG. 3). Also, the size of colon cancer tissue was reduced by shedding microvesicles derived from *S. enteritidis* (FIG. 4).

Example 3

In Vivo Anticancer Activity of Gram-Positive Bacterial Cell-Derived Shedding Microvesicles For use in this experiment, microvesicles that were spontaneously shed from Gram-positive bacteria were isolated. The Gram-positive bacteria *Staphylococcus aureus* and *Lactobacillus acidophilus* were used as sources of microvesicles. Bacteria were inoculated into 100 mL of a nutrient broth in an Erlenmeyer flask and cultured at 37° C. for 6 hrs. Of the culture, 8 mL was transferred into 600 mL of a nutrient broth in a 2 L Erlenmeyer flask and cultured at 37° C. for 5 hrs to an optical density of 1.5 (at 600 nm). The resulting culture was divided into 500 mL high speed centrifuge tubes before centrifugation at 10,000×g and 4° C. for 20 min. The supernatant was forced to pass once through a membrane filter with a pore size of 0.45 μm, and then concentrated 25-fold using a Quixstand system equipped with a membrane having a molecular weight cut-off of 100 kDa. The concentrate was passed once through a membrane filter with a pore size of 0.22 μm, and divided into 70 mL ultracentrifuge tubes, followed by ultracentrifugation at 150,000×g and 4° C. for 3 hrs to afford bacteria cell-derived shedding microvesicles as a precipitate. This was suspended in PBS.

The shedding microvesicles derived from *S. aureus* and *Lactobacillus acidophilus* were assayed for anticancer activity. A mouse colon 26 cell line was subcutaneously injected at a dose of $1 \times 10^6$ cells into mice, and cultured. After one week, a PBS solution containing 10 μg of each of the Gram-positive bacterial cell-derived microvesicles was injected at a dose of 100 μl twice a week via the tail vein into the mice which were divided into groups, each consisting of three. On day 23 after the transplantation of cancer cells, the sizes of colon cancer tissue were monitored. The volume of cancer tissue was calculated by the equation $V=l \times s^2/2$, wherein l is a length of the longest axis of a tumor and s is a length of the axis perpendicular to the longest axis.

Figure 5:
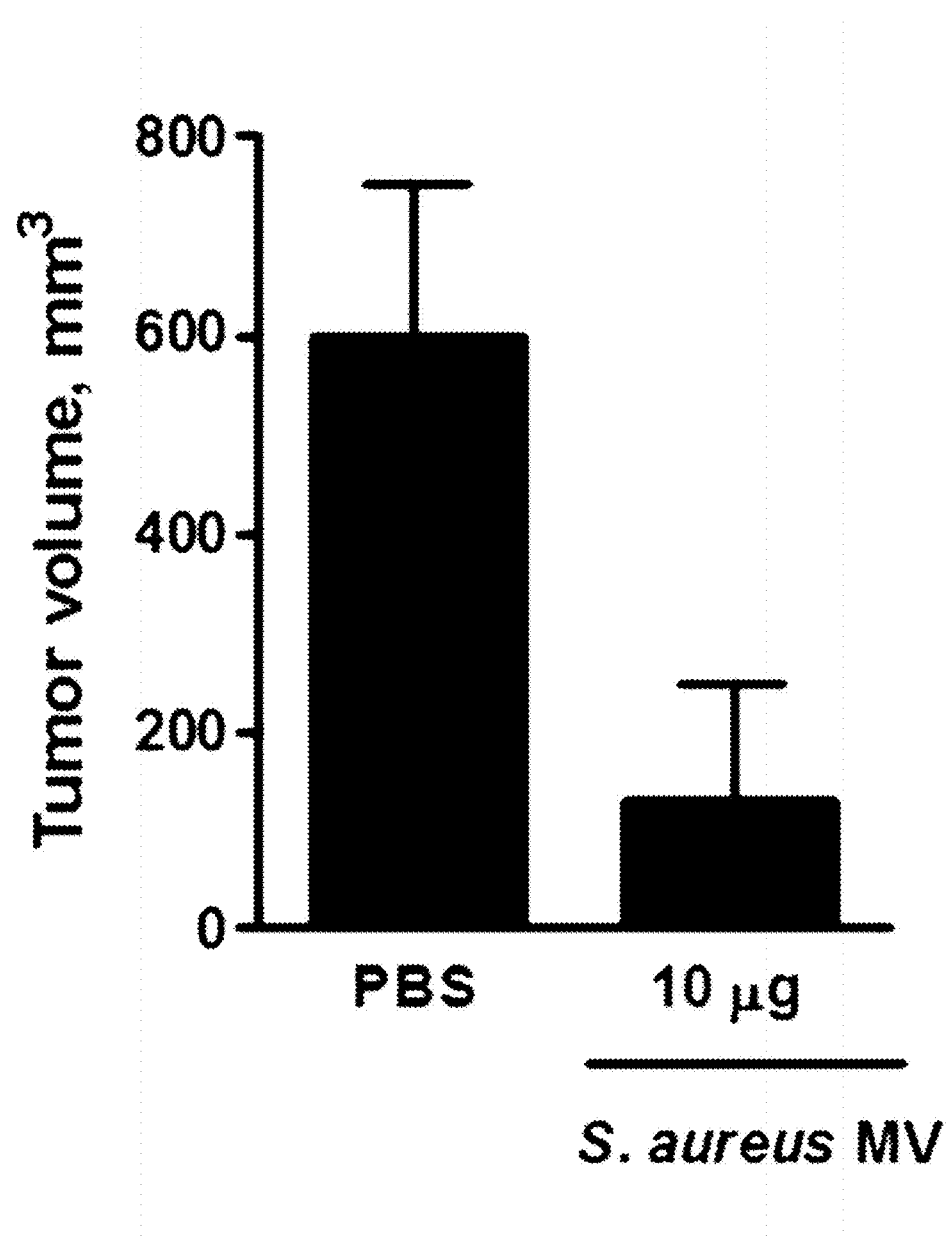
FIG. 5 is a graph showing the inhibition of shedding microvesicles derived from Gram-positive bacterium *S. aureus* (S. aureus MV) against the growth of cancer tissues (tumor volume) in animal models of colon cancer.
Figure 6:
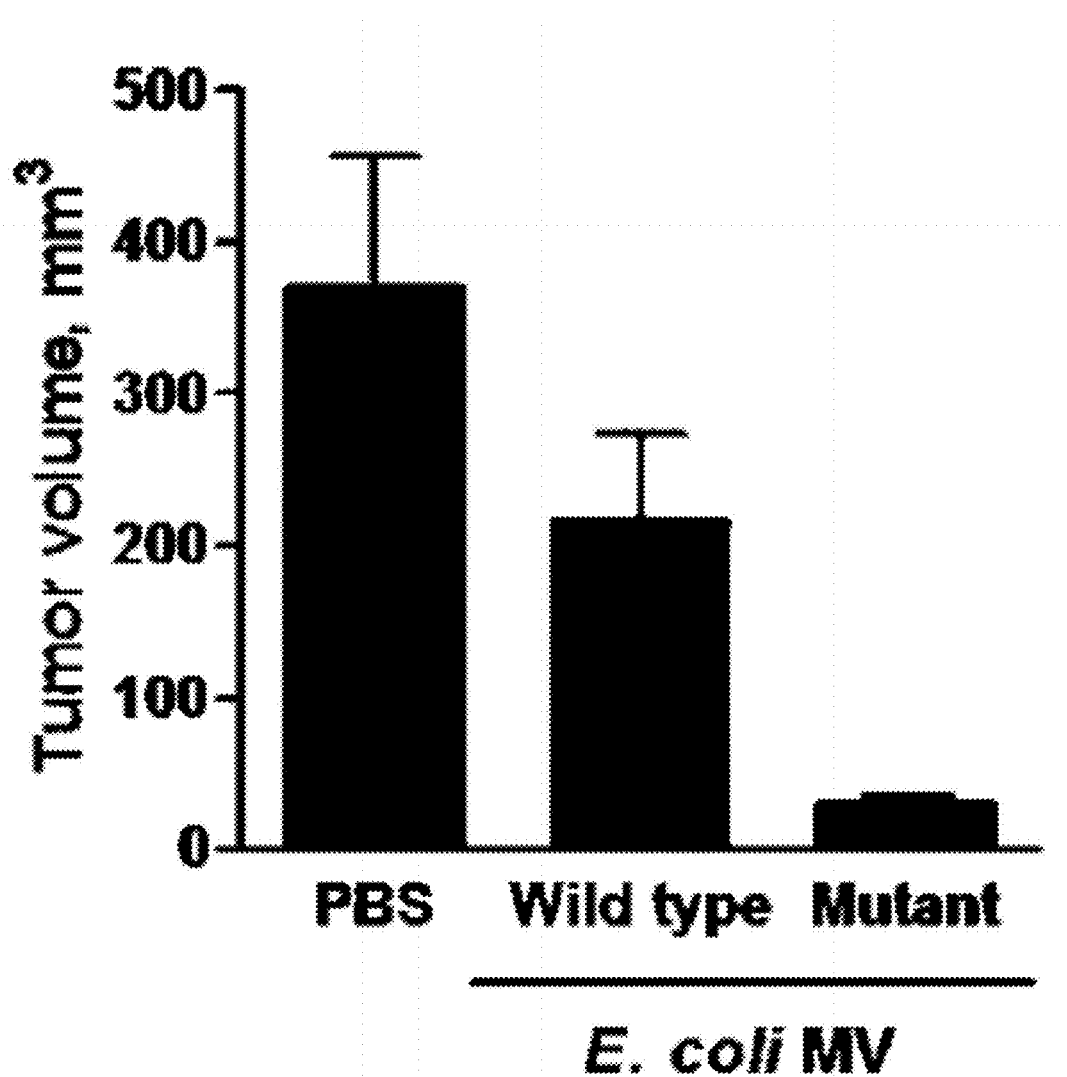
FIG. 6 is a graph showing the inhibition of shedding microvesicles derived from Gram-positive bacterium *L. acidophilus* (L. acidophilus MV) against the growth of cancer tissues (tumor volume) in animal models of colon cancer.

After the subcutaneous transplantation, the volume measurements of colon cancer tissues were as shown in FIGS. 5 and 6. As can be seen in the graphs, a significant reduction in the size of colon cancer tissues was obtained after shedding microvesicles derived from S. aureus (FIG. 5) or L. acidophilus (FIG. 6) were administered, compared to the control PBS.

Example 4

In Vivo Anticancer Activity of Shedding Microvesicles Derived from Transformed Gram-Negative Bacteria The following experiment was carried out with shedding microvesicles which were obtained in the same manner as in Example 2, with the exception that E. coli transformed to have reduced lipopolysaccharide toxicity (msbB mutant) was employed.

A mouse colon 26 cell line was subcutaneously injected at a dose of $1 \times 10^6$ cells into mice, and cultured. After one week, PBS or a PBS solution containing 1 mg of the shedding microvesicles derived from wild-type E. coli or the mutant E. coli transformed to have reduced lipopolysaccharide toxicity was injected at a dose of 100 mL twice a week via the tail vein into the mice which were divided into groups of three. On day 23 after the transplantation of cancer cells, the sizes of colon cancer tissue were monitored. The volume of cancer tissue was calculated by the equation $V=l \times s^2/2$, wherein l is a length of the longest axis of a tumor and s is a length of the axis perpendicular to the longest axis.

Figure 7:
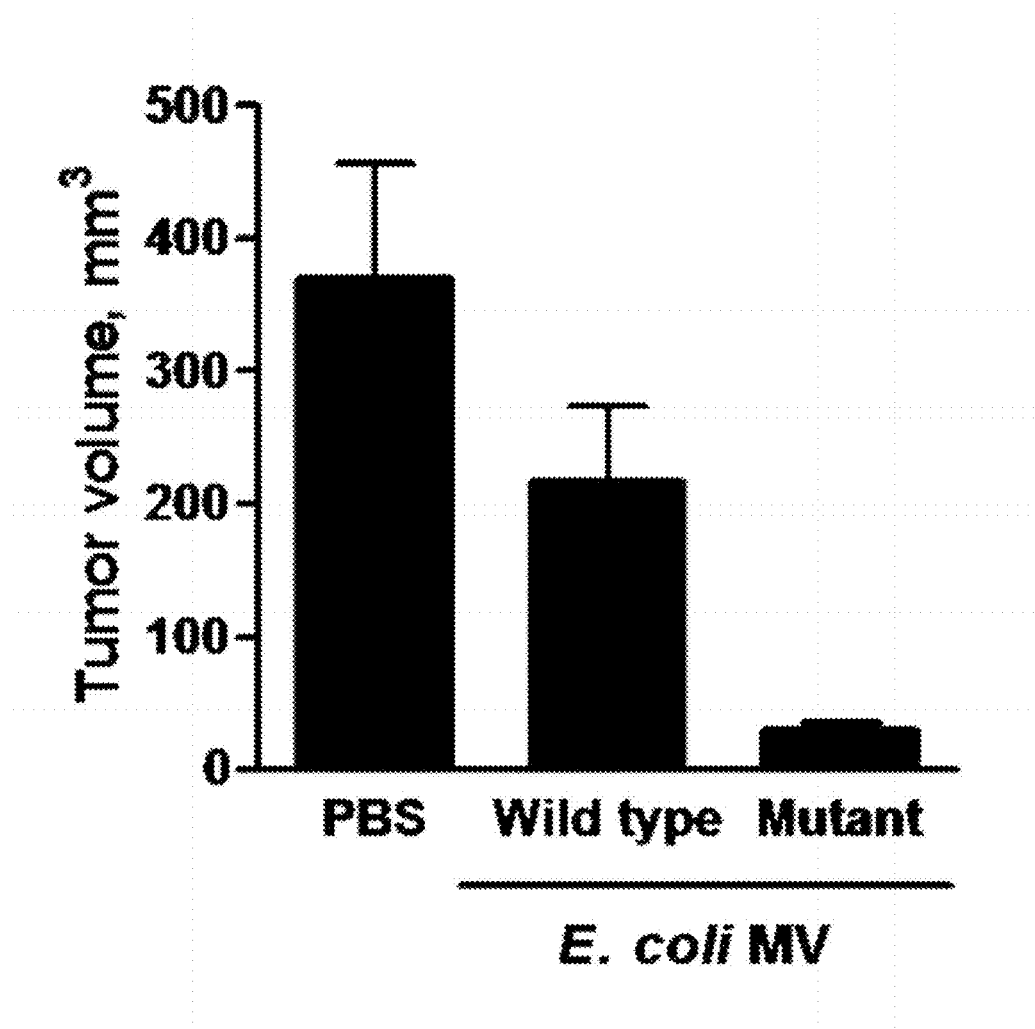
FIG. 7 is a graph showing anticancer effects of shedding microvesicles (*E. coli* MV) derived from wild-type *E. coli* and mutant *E. coli* transformed to have reduced toxicity of lipopolysaccharides on the growth of cancer tissues (tumor volume) in animal models of colon cancer.

After the subcutaneous transplantation, the volume measurements of colon cancer tissues were as shown in FIG. 7. As can be seen in FIG. 7, the mouse group, when administered with the shedding microvesicles derived from the mutant E. coli which had been transformed to have reduced LPS toxicity, was observed to have a significantly decrease in tumor size, compared to the control administered with PBS only. Also, the colon cancer of the mutant group was much smaller in size than that of the wild-type group.

Example 5

In Vivo Anticancer Activity of Shedding Microvesicles Derived from Transformed Gram-Positive Bacteria The following experiment was carried out with shedding microvesicles which were obtained in the same manner as in Example 3, with the exception that S. aureus coli transformed to have reduced toxicity of lipoteichoic acid (LTA mutant) was employed.

A mouse colon 26 cell line was subcutaneously injected at a dose of $1 \times 10^6$ cells into mice, and cultured. After one week, PBS or a PBS solution containing 10 μg of the shedding microvesicles derived from wild-type S. aureus or the mutant S. aureus transformed to have reduced toxicity of lipoteichoic acid was injected at a dose of 100 μL twice a week via the tail vein into the mice which were divided into groups, each consisting of three. On day 23 after the transplantation of cancer cells, the sizes of colon cancer tissue were monitored. The volume of cancer tissue was calculated by the equation $V=l \times s^2/2$, wherein l is a length of the longest axis of a tumor and s is a length of the axis perpendicular to the longest axis.

Figure 8:
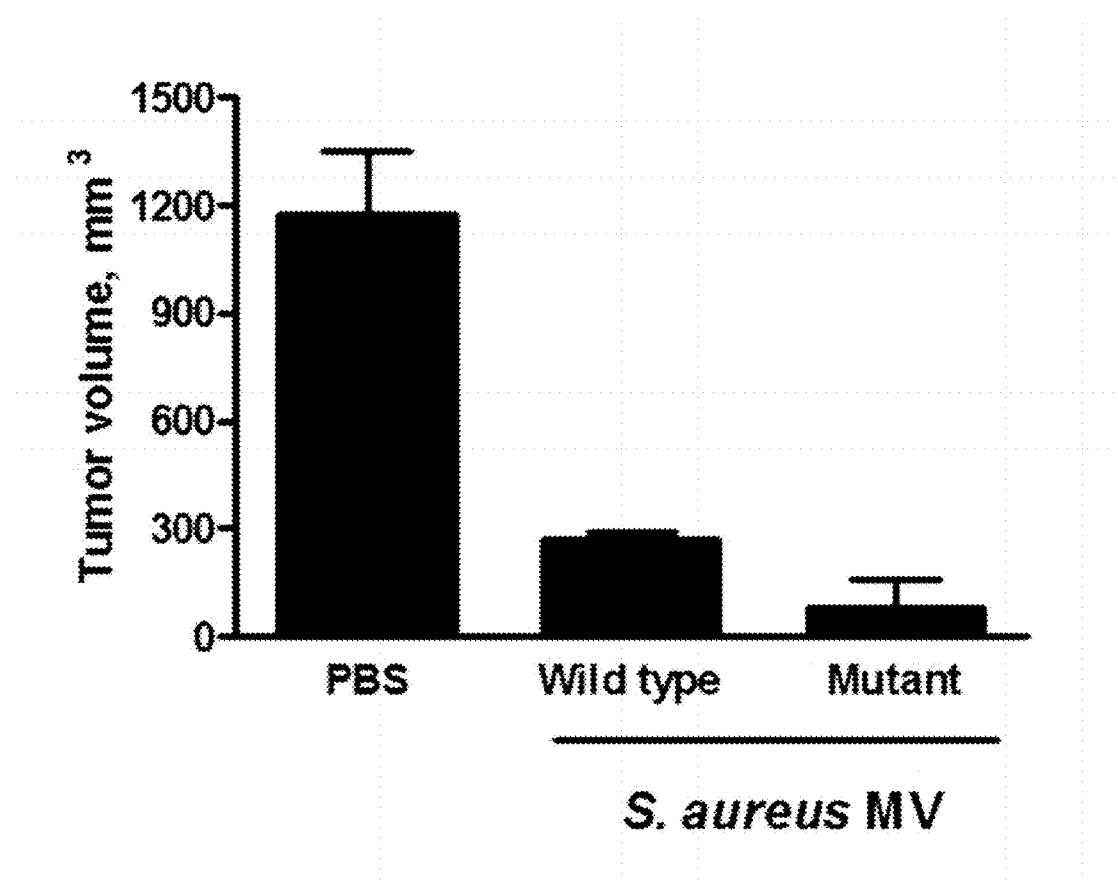
FIG. 8 is a graph showing anticancer effects of shedding microvesicles (*S. aureus* MV) derived from wild-type *S. aureus* and mutant *S. aureus* transformed to have reduced toxicity of lipoteichoic acid on the growth of cancer tissues (tumor volume) in animal models of colon cancer.

After the subcutaneous transplantation, the volume measurements of colon cancer tissues were as shown in FIG. 8. As can be seen in FIG. 8, the mouse group, when administered with the shedding microvesicles derived from the mutant S. aureus which had been transformed to have reduced toxicity of lipoteichoic acid, was observed to significantly decrease in tumor size, compared to the control administered with PBS only. Also, the colon cancer of the mutant group was much smaller in size than that of the wild-type group.

Example 6

In Vivo Therapeutic Effect of Shedding Microvesicles Derived from Transformed Gram-Negative Bacteria on Metastasized Cancer The following experiment was carried out with shedding microvesicles which were obtained in the same manner as in Example 2, with the exception that E. coli transformed to have reduced lipopolysaccharide toxicity was employed.

The mouse melanoma cell line (B16BL6) was injected at a dose of $1 \times 10^5$ cells into mice via the tail vein and cultured. After three days, PBS, or PBS containing 1 μg of the shedding microvesicles derived from E. coli that had been transformed to have reduced LPS toxicity, was injected at a dose of 100 μl in a day for 10 days via the tail vein into mouse groups, each consisting of three mice. On day 14 after the injection of the melanoma cells, the lungs were excised from the mice to count melanoma colonies metastasized to the lung.

Figure 9:
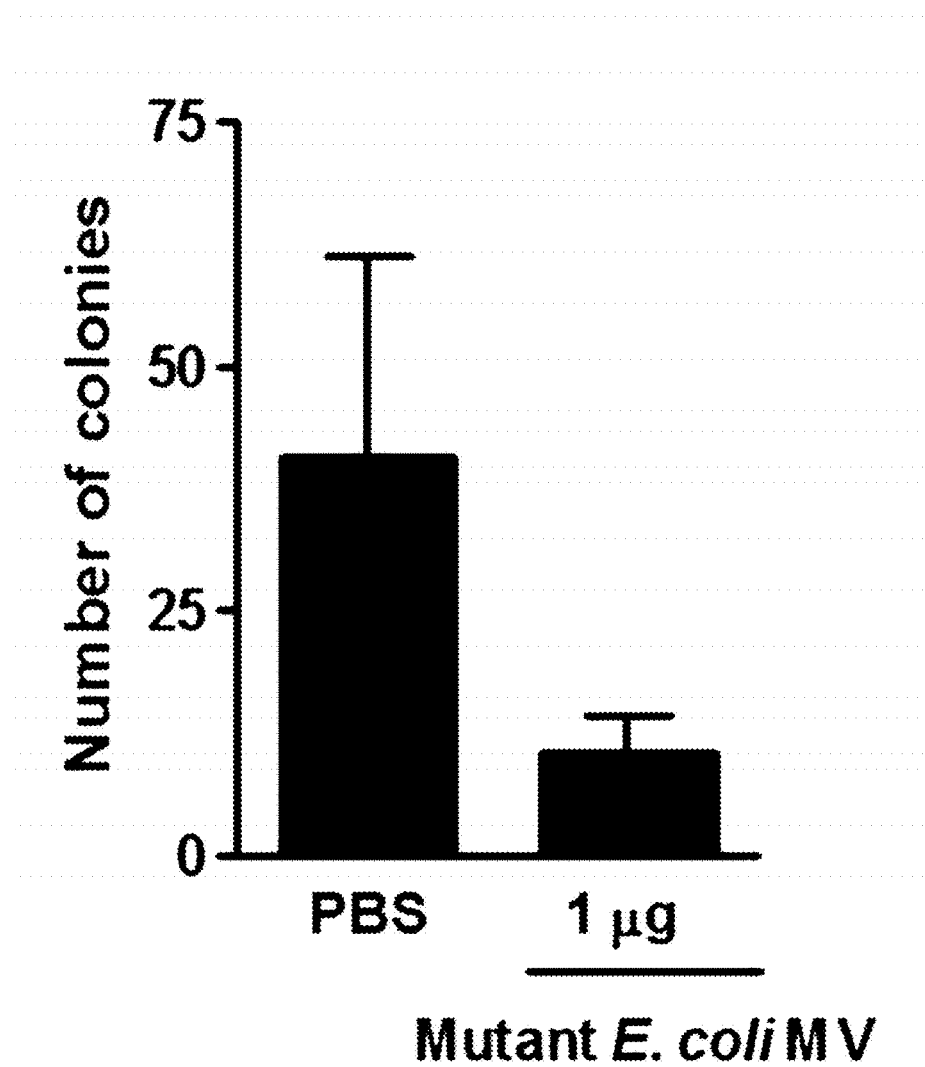
FIG. 9 is a graph showing anticancer effects of shedding microvesicles (*E. coli* MV) derived from mutant *E. coli* transformed to have reduced toxicity of lipopolysaccharides on the growth of cancer tissues (number of colony) in animal models of metastasized melanoma.

FIG. 9 is a graph showing numbers of melanoma colonies metastasized to the lung in each mouse group of three. As can be seen in FIG. 9, the mice administered with the microvesicles derived from E. coli that had been transformed to have reduced LPS toxicity were found to have much fewer melanoma colonies metastasized to the lung, compared to the PBS control.

Example 7

Anticancer Activity upon Co-Administration of Bacterial Cell-Derived Shedding Microvesicles and Drug From several centuries ago, the role of inflammation in oncogenesis has been suggested. In recent years, intensive attention have been paid to the research result that inflammatory reactions resulting from VEGF/IL-6-mediated signaling, STAT3 (signal transducer and activator of transcription 3) signaling, and Th17 immune responses play an important role in the onset and progression of cancer. In addition, aspirin was reported to reduce colorectal cancer risk. The present inventors have recently found that aspirin suppresses Th17-mediated inflammation. In this example, the anticancer activity of bacterial cell-derived microvesicles was examined when they were co-administered together with a drug suppressive of Th17 immune responses. In this regard, shedding microvesicles derived from E. coli that had been transformed to have reduced LPS activity were obtained in the same manner as in Example 2, and administered in combination with aspirin, a drug suppressive of the immune response of Th17.

A mouse colon 26 cell line was subcutaneously injected at a dose of $1 \times 10^6$ cells into mice, and cultured. After one week, PBS, a PBS solution containing 18 mg/kg of aspirin, a PBS solution containing 0.1 μg of the bacterial cell-derived microvesicles, or a PBS solution containing 0.1 μg of the bacterial cell-derived microvesicles and 18 mg/kg of aspirin was injected at a dose of 100 μL twice a week via the tail vein into mouse groups, each consisting of four. On day 23 after the transplantation of cancer cells, the sizes of colon cancer tissue were monitored. The volume of cancer tissue was calculated by the equation $V=l\times s^2/2$, wherein l is a length of the longest axis of a tumor and s is a length of the axis perpendicular to the longest axis.

Figure 10:
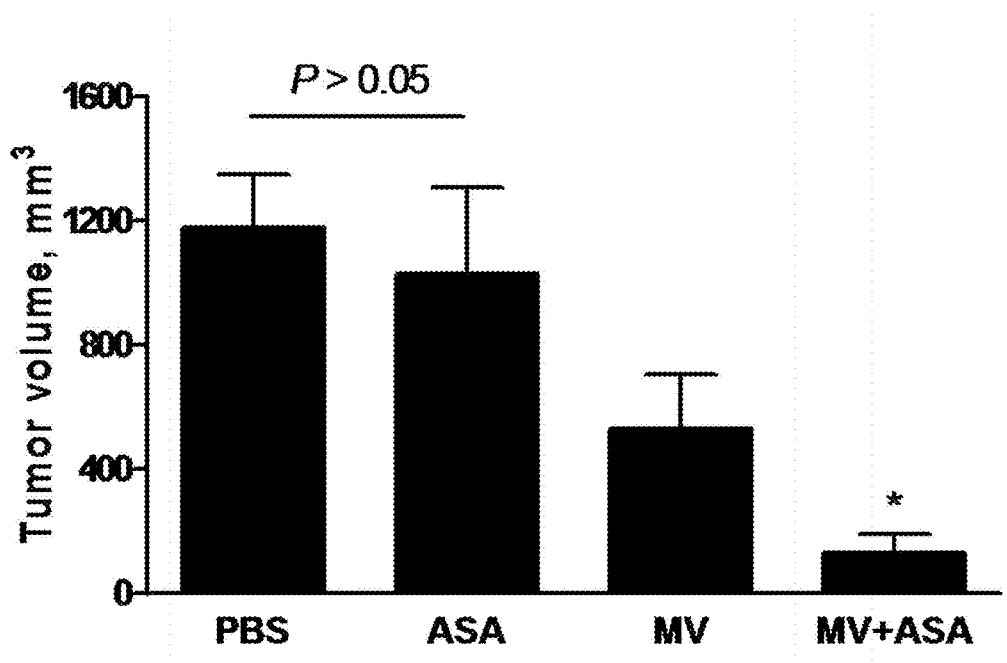
FIG. 10 is a graph showing anticancer activity upon co-administration of shedding microvesicles (MV) derived from mutant *E. coli* transformed to have reduced toxicity of lipopolysaccharides, and aspirin (ASA) to animal models of colon cancer.

After the subcutaneous transplantation, the volume measurements of colon cancer tissues were as shown in FIG. 10. As can be seen in FIG. 10, there was no differences in the size of colon tumors between the group administered with aspirin alone and the control group administered with PBS alone. That is, the anticancer effect of aspirin was not observed. However, the size of colon tumors was significantly further reduced when the shedding microvesicles derived from *E. coli* that had been transformed to have reduced LPS toxicity were administered in combination with aspirin than alone.

Taken together, the data obtained above demonstrate that when co-administered together with a drug suppressive of the immune response of Th17, such as aspirin, the bacterial cell-derived shedding microvesicles of the present invention exerts greater anticancer activity.

Example 8

Loading of Anticancer Drug to Gram-Negative Bacterial Cell-Derived Shedding Microvesicles For use in the following experiments, shedding microvesicles derived from *E. coli* that had been transformed to have reduced LPS activity were obtained in the same manner as in Example 2.

The shedding microvesicles were mixed at a ratio of 1:1 with 0.4 mg/ml of doxorubicin and incubated at 4° C. for 12 hrs. Thereafter, the suspension was ultracentrifuged at 150,000×g and 4° C. for 3 hrs to separate shedding microvesicles from doxorubicin-loaded microvesicles. The doxorubicin-loaded microvesicles were incubated with DiO, a liphophilic trace with green fluorescence that can bind to cell membranes. DiO-labeled microvesicles were instilled on a cover glass, followed by observation under a confocal microscope to examine whether doxorubicin was loaded to the shedding microvesicles. The fluorescence images are given in FIG. 11.

Figure 11:
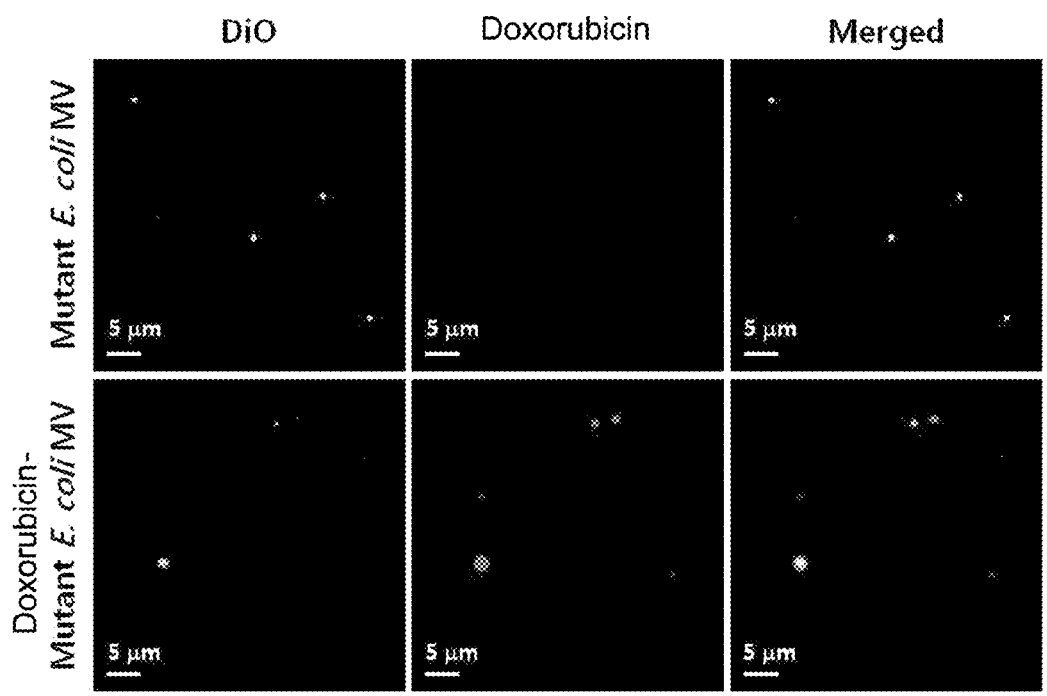
FIG. 11 shows images of doxorubicin loaded to green fluorescent (DiO)-labeled shedding microvesicles derived from mutant *E. coli* transformed to have reduced toxicity of lipopolysaccharides (mutant *E. coli* MV).

As can be seen in FIG. 11, doxorubicin which appeared fluorescent red were loaded to the shedding microvesicles observed to be fluorescent green. From these results, it was understood that a therapeutic or diagnostic drug can be effectively loaded to bacterial cell-derived microvesicles.

Example 9

In Vitro Anticancer Activity of Anticancer Drug-Loaded, Bacterial Cell-Derived Microvesicles Anticancer agent-loaded, bacterial cell-derived microvesicles were assayed for anticancer activity to examine whether the anticancer agent load has an influence on the activity of the microvesicles themselves. Doxorubicin was used as an anticancer agent.

For use in the following experiments, shedding microvesicles derived from *E. coli* that had been transformed to have reduced LPS activity were obtained in the same manner as in Example 8.

A mouse colon 26 cell line was seeded at a density of $5\times10^4$ cells into 24-well plates and cultured overnight. The cancer cells in each well were treated for 6 hrs with 1 mL of PBS or a PBS solution containing the bacterial cell-derived microvesicles loaded with or without doxorubicin, and then incubated for 18 hrs. Viable mouse colon cancer 26 cells were counted under a microscope, and the results are given in FIG. 12.

Figure 12:
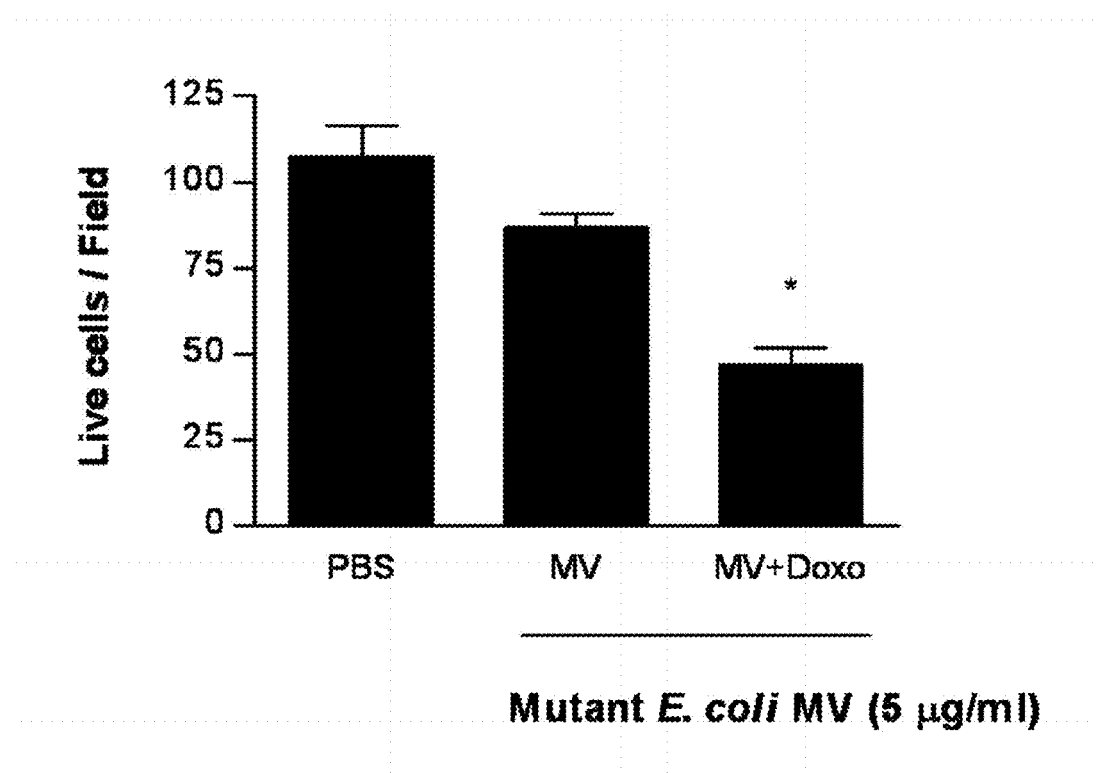
FIG. 12 is a graph showing the anticancer activity of doxorubicin (Doxo)-loaded shedding microvesicles (MV+Doxo) derived from mutant *E. coli* transformed to have reduced toxicity of lipopolysaccharides against a mouse colon 26 cell line.

As can be seen in FIG. 12, doxorubicin-loaded, bacterial cell-derived microvesicles exerted greater inhibitory activity against cancer cells than did bacterial cell-derived microvesicles void of doxorubicin.

From this result, it is apparent that the anticancer activity of the anticancer drug-loaded, bacterial cell-derived microvesicles is contributed by not only the bacterial cell-derived microvesicles, but also by the loaded anticancer drug and thus is greater than that of the bacterial cell-derived microvesicles alone.

Example 10

Effect of Lipopolysaccharide Inhibitor on Side Effects of Bacterial Cell-Derived Microvesicles In relation to the side effects of bacterial cell-derived microvesicles, Lipopolysaccharide, a component of bacterial cell-derived microvesicles, is known to play an important role one the onset of sepsis. Hence, an inhibitor of lipopolysaccharides that the microvesicles retain was examined for effects on the side effects of the microvesicles. In this experiment, polymyxin B was employed as an LPS inhibitor.

*E. coli*-derived shedding microvesicles were constructed according to the method described in Example 2. PBS, a PBS solution 25 μg of *E. coli*-derived shedding microvesicles, a PBS solution containing 25 μg of *E. coli*-derived shedding microvesicles plus 250 μg of polymyxin B were intraperitoneally injected at a dose of 100 μl into respective mouse groups, after which the survival rates of the mice were monitored at regular intervals of 12 hrs for 120 hrs. The results are given in FIG. 13.

Figure 13:
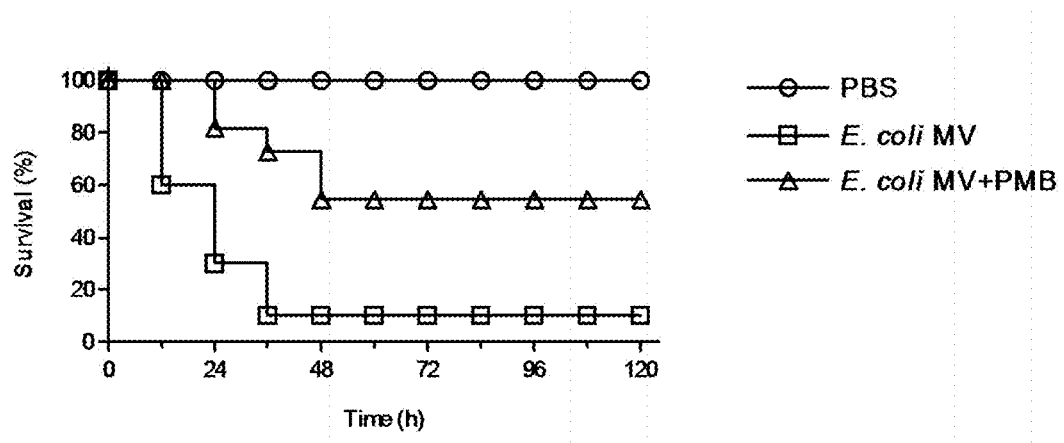
FIG. 13 is a graph showing the effect of polymyxin B (PMB) on the side effect (death caused by systemic inflammation) of *E. coli*-derived shedding microvesicles (*E. coli* MV).

As can be seen in FIG. 13, the survival rate of the mice was % at 120 hrs after administration with a PBS solution containing 25 μg of *E. coli*-derived shedding microvesicles, but increased to 55% in the same period of time after administration with a PBS solution containing 25 μg of *E. coli*-derived shedding microvesicles plus 250 μg of polymyxin B.

From the result, it is understood that an inhibitory drug of the activity of lipopolysaccharides of *E. coli*-derived microvesicles effectively suppresses the side effects of the bacterial cell-derived microvesicles.

Example 11

Difference in Side Effect between Wild-Type and Transformed Gram-Negative Bacterial Cell-Derived Microvesicles The side effects of bacterial cell-derived microvesicles to which lipopolysaccharides, a component of Gram-negative bacterial cell-derived microvesicles, make contribution were examined using microvesicles derived from *E. coli* that had been transformed to have reduced toxicity of lipopolysaccharide, a component of the microvesicles. In this experiment, the msbB mutant was employed as the *E. coli* transformed to have reduced toxicity of lipopolysaccharides.

Shedding microvesicles were constructed in the same manner as in Example 2 from *E. coli* transformed to have reduced toxicity of lipopolysaccharides. PBS, a PBS solution 25 μg of shedding microvesicles derived from wild-type *E. coli*, and a PBS solution containing 25 μg of shedding microvesicles derived from the mutant *E. coli* were intraperitoneally injected at a dose of 100 μl into respective mouse groups, after which the survival rates of the mice were monitored at regular intervals of 12 hrs for 120 hrs. The results are given in FIG. 14.

Figure 14:
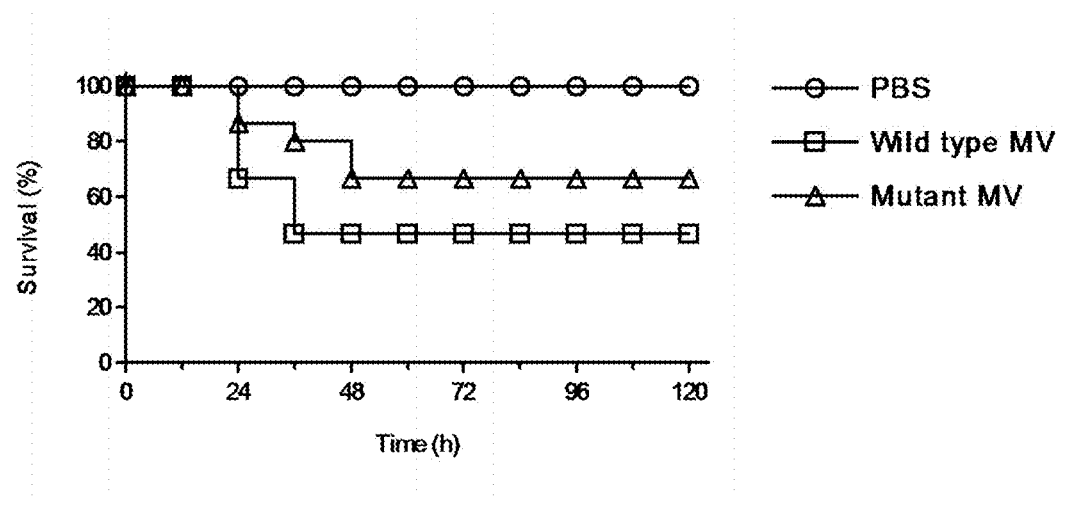

As can be seen in FIG. 14, the survival rate of the mice was 45% at 120 hrs after administration with a PBS solution containing 25 μg of the wild-type *E. coli*-derived shedding microvesicles, but increased to 65% at the same period of time after administration with a PBS solution containing 25 μg of the mutant *E. coli*-derived shedding microvesicles.

From the result, it is understood that the side effects of bacterial cell-derived microvesicles can be effectively diminished when the microvesicles are derived from a mutant *E. coli* in which the activity of lipopolysaccharides is removed by modifying a gene responsible for the production of lipopolysaccharides, one of the microvesicle components causing the side effects, compared to when the microvesicles are derived from wild-type *E. coli*.

Example 12

Remission of Side Effects caused by Microvesicles Derived from Transformed Gram-Negative Bacteria In order to examine the side effects which might be generated upon the intravenous injection of bacterial cell-derived microvesicles, shedding microvesicles derived from *E. coli* that had been transformed to have reduced toxicity of lipopolysaccharides were employed. As indices for the side effects that might be generated upon intravenous injection, the number of platelets, blood coagulation, and hemolysis were examined.

For use in this assay, shedding microvesicles were isolated in the same manner as in Example 2, from the *E. coli* transformed to have reduced toxicity of lipopolysaccharides.

Mouse colon 26 cell line was subcutaneously injected at a dose of $1\times10^6$ cells into mice, and cultured. After one week, PBS or a PBS solution containing 5 μg of shedding microvesicles derived from *E. coli* that had been transformed to have reduced toxicity of lipopolysaccharides was injected via the tail vein into mouse groups, each consisting of two mice. After 3 or 6 hrs after, blood samples were taken from the mice.

Platelets play an important role in the formation of blood clots. To examine the effect of the intravenous injection of bacterial cell-derived microvesicles on the number of platelets, the following experiment was carried out. The blood samples were 100-fold diluted in a dilution fluid (Rees-Ecker fluid), and incubated for 10 min at room temperature in a hemocytometer before counting platelets under an optical microscope. The results are given in FIG. 15.

Figure 15:
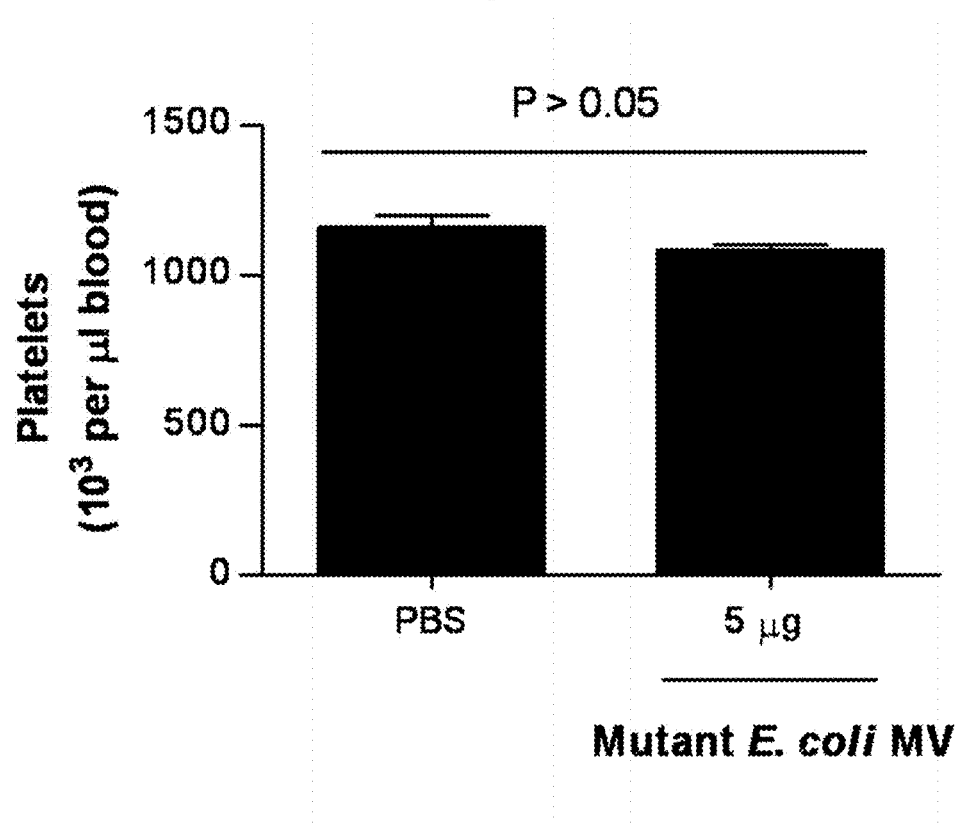
FIG. 15 is a graph showing a change in the number of platelets after microvesicles derived from mutant *E. coli* transformed to have reduced toxicity of lipopolysaccharides (mutant *E. coli* MV) are intravenously injected.

Even when injected intravenously, as can be seen in FIG. 15, shedding microvesicles derived from *E. coli* that had been transformed to have reduced activity of lipopolysaccharides had no influences on platelets, which play an important role in blood coagulation.

D-dimer is a fibrin degradation product, a small protein fragment present in the blood after a blood clot is degraded by fibrinolysis, and thus serves as a diagnostic criterion for disseminated intravascular coagulation. To examine the intravascular coagulation caused by the shedding microvesicles derived from *E. coli* that had been transformed to have reduced toxicity of lipopolysaccharides, the following experiment was carried out. The blood samples taken from Example 12 were centrifuged 1,300×g for 10 min. The blood plasma thus obtained was 3-fold diluted and plated into 96-well plates coated with a capture antibody recognizing D-dimer. Then, a hydrogen peroxidase-conjugated detection antibody specific for D-dimer was added. Afterwards, a color was developed with the substrate BM-POD, and the results are given in FIG. 16.

Figure 16:
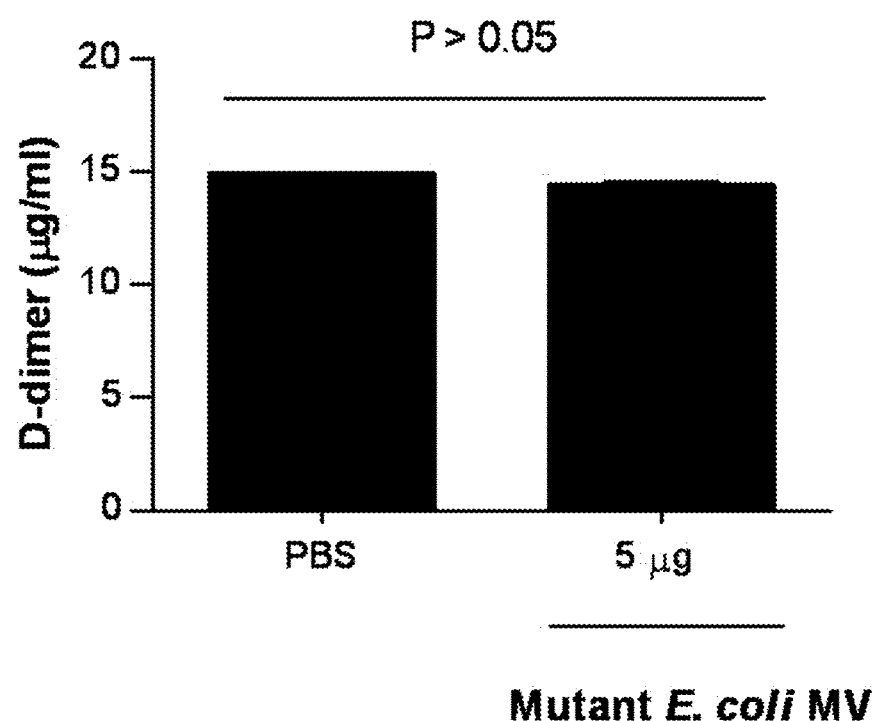
FIG. 16 is a graph showing a change in the level of D-dimer after microvesicles derived from mutant *E. coli* transformed to have reduced toxicity of lipopolysaccharides (mutant *E. coli* MV) are intravenously injected.

Even when injected intravenously, as can be seen in FIG. 16, shedding microvesicles derived from *E. coli* that had been transformed to have reduced activity of lipopolysaccharides did not activate the coagulation mechanism.

The hemolysis caused by the shedding microvesicles derived from *E. coli* that had been transformed to have reduced toxicity of lipopolysaccharides was examined in the following experiment. PBS, and a PBS solution containing 1 μg/ml or 2 μg/ml of the mutant *E. coli*-derived shedding microvesicles were dropwise added in an amount of 10 μl to a blood agar plate, and incubated for 12 hrs at 37° C. The results are shown in FIG. 17.

Figure 17:
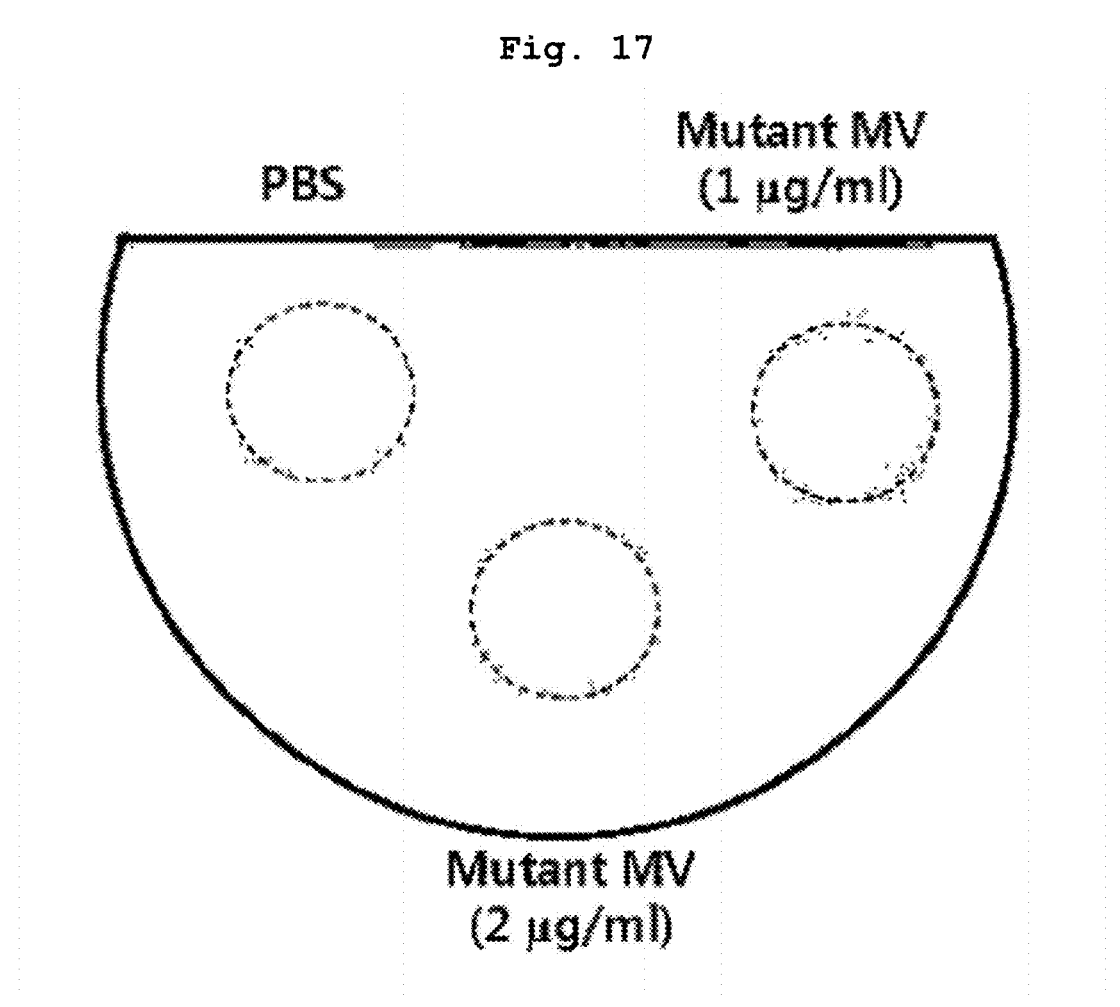

As shown in FIG. 17, the shedding microvesicles derived from the *E. coli* that had been transformed to have reduced toxicity of lipopolysaccharides cannot destroy erythrocytes.

As is apparent from data of FIGS. 15 to 17, the shedding microvesicles derived from *E. coli* that that had been transformed to have reduced toxicity of lipopolysaccharides do not cause, even when injected intravenously, a decrease in the number of platelets, blood coagulation, and hemolysis. Therefore, the side effects of bacterial cell-derived microvesicles can be effectively reduced when the bacteria have been transformed to have reduced toxicity of lipopolysaccharides.

Example 13

Difference in Side Effect between Wild-Type and Transformed Gram-Positive Bacterial Cell-Derived Microvesicles Lipoteichoic acid is known to induce inflammation through specific immune responses, and thus contributes to the side effects of Gram-positive bacterial cell-derived microvesicles because it is a component of the cell wall of Gram-positive bacteria. Hence, microvesicles derived from bacteria that had been transformed to lack a gene involved in the biosynthesis of lipoteichoic acid were used to evaluate the role of lipoteichoic acid in the side effects of Gram-positive bacterial cell-derived microvesicles. In this experiment, the LTA mutant was employed as the *S. aureus* transformed to remove lipoteichoic acid from the cell wall.

Shedding microvesicles were constructed in the same manner as in Example 3 from *S. aureus* transformed to have reduced toxicity of lipoteichoic acid. After being isolated from the abdominal cavity of mice, macrophages ($2.5\times10^5$ cells) were incubated for 12 hrs with 0.5 mL of each of PBS, a PBS containing 0.1 μg/ml of wild-type *S. aureus*-derived shedding microvesicles, and a PBS solution containing 0.1 μg/ml of the mutant *S. aureus*-derived shedding microvesicles, and the conditioned media were centrifuged at 500×g for 5 min.

Each well of 96-well plates coated with an IL-6 capture antibody was blocked for 1 hr with 100 μl of 1% BSA (bovine serum albumin). The conditioned media was diluted by half, added to the plates, and incubated at room temperature for 2 hours and then for an additional 2 hrs in the presence of a biotinylated detection antibody against IL-6. The plates were washed with 1% BSA, and incubated for 30 min with streptavidin-POD, followed by developing a color with the substrate BM-POD. The results are given in FIG. 18.

Figure 18:
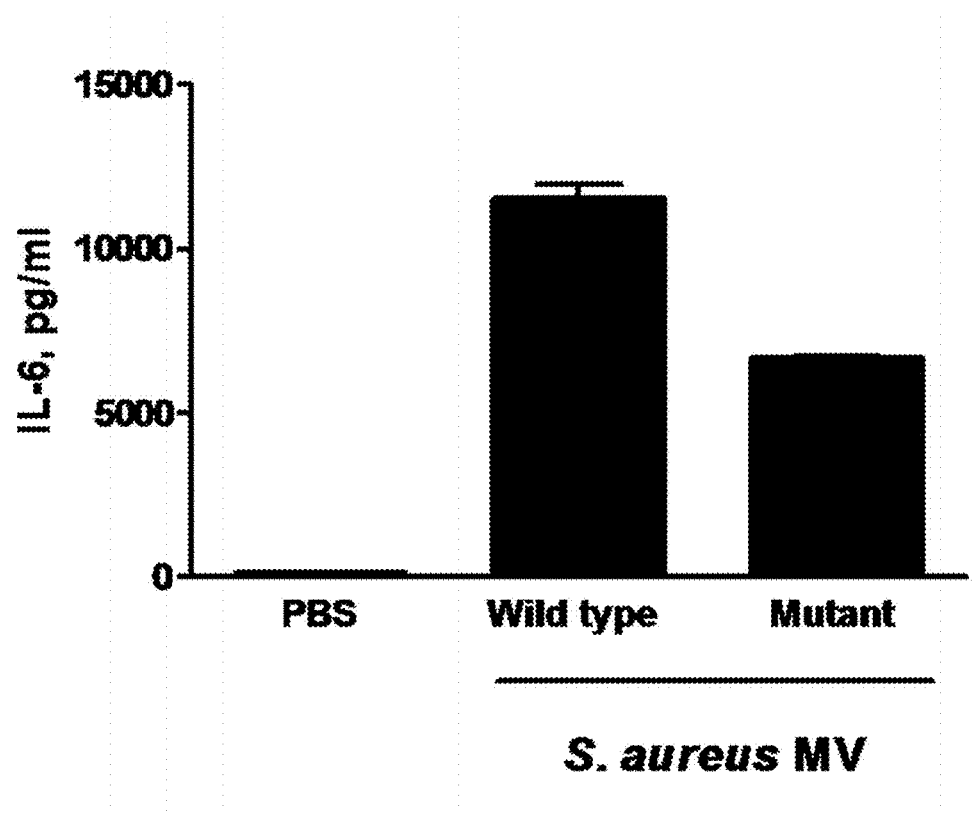
FIG. 18 is graph showing side effects (IL-6 release from inflammatory cells) of shedding microvesicles (*S. aureus* MV) derived from wild-type *S. aureus* and mutant *S. aureus* transformed to have reduced toxicity of lipoteichoic acid.

As is apparent from the data of FIG. 18, the level of IL-6 was reduced when shedding microvesicles derived from *S. aureus* that had been transformed to have reduced toxicity of lipoteichoic acid were administered, compared to wild-type *S. aureus*-derived shedding microvesicles.

From the result, it is understood that the side effects of bacterial cell-derived microvesicles can be effectively diminished when the microvesicles are derived from mutant bacteria in which the activity of lipoteichoic acid is reduced by modifying a gene responsible for the production of lipoteichoic acid, one of the microvesicle components causing the side effects, compared to when the microvesicles are derived from the wild-type.

Example 14

Side Effects of Bacterial Cell-Derived Microvesicles upon Co-Administration with Anti-Inflammatory and/or Anti-Coagulant Drug Important among the side effects of bacterial cell-derived microvesicles are a microvesicle-triggered immune response that induces the release of inflammatory mediators, causing topical or systemic inflammatory responses, and a microvesicle-caused coagulation that leads to thromboembolism or disseminated intravascular coagulation. In this experiment, aspirin was employed as an anti-inflammatory and anti-coagulant drug with the aim of reducing the side effects of bacterial cell-derived microvesicles.

A mouse colon 26 cell line was subcutaneously injected at a dose of $1 \times 10^6$ cells into mice, and cultured. Shedding microvesicles were isolated in the same manner as in Example 2 from *E. coli* that had been transformed to have reduced toxicity of lipopolysaccharides. After one week, PBS, a PBS solution containing 18 mg/kg of aspirin, a PBS solution containing 0.1 µg of the bacterial cell-derived microvesicles, and a PBS solution containing 0.1 µg of the bacterial cell-derived microvesicles plus 18 mg/kg of aspirin were injected at a dose of 100 µl via the tail vein into respective groups of four twice a week. Six hrs after the fifth injection, 0.2 ml of a blood sample was taken from the eye of each mouse, and placed in an anticoagulant tube containing 50 mM EDTA (ethylenediaminetetraacetic acid). Of the blood sample, 10 µl was mixed with 90 µl of 1% HCl, and stored at room temperature for 7 min. White blood cells, indicative of systemic inflammation, in 10 µl of the mixture were counted using a hematocytometer. The result is given in FIG. 19.

Figure 19:
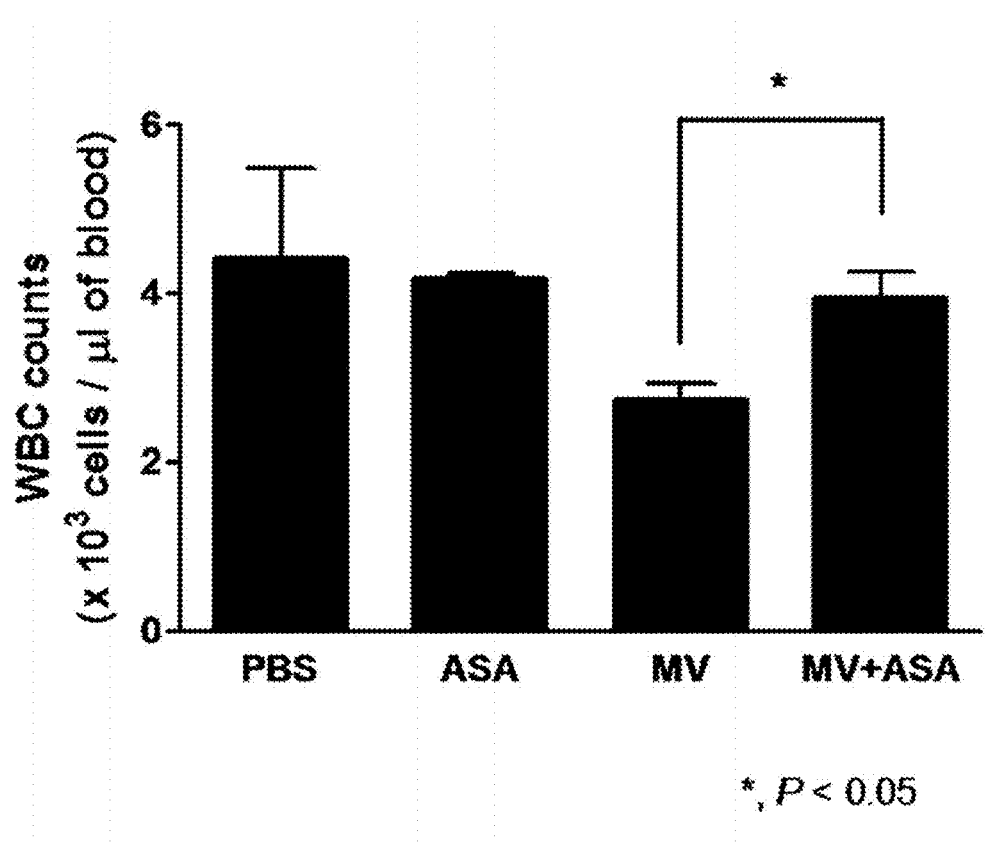
FIG. 19 is a graph showing the effect of the co-administration of aspirin (ASA) on the side effect (WBC count, indicative of systemic inflammation) of microvesicles derived from mutant *E. coli* transformed to have reduced toxicity of lipopolysaccharides (MV) in animal models of colon cancer.

As can be seen in FIG. 19, there were no differences in the level of white blood cells between the groups administered with aspirin alone and the group administered with PBS. The administration of the microvesicles derived from *E. coli* that had been transformed to have reduced toxicity of lipopolysaccharides reduced the level of white blood cells. However, the level of white blood cells returned to normal when aspirin was administered in combination with the microvesicles derived from *E. coli* that had been transformed to have reduced toxicity of lipopolysaccharides.

From the result, it is understood that co-administration of bacterial cell-derived microvesicles and an anti-inflammatory and/or anti-coagulant drug can effectively reduce the side effect (leucopenia) of bacterial cell-derived microvesicles.

Example 15

Drug Delivery of Bacterial Cell-Derived Microvesicles to Cancer Tissue

In this experiment, shedding microvesicles derived from *E. coli* that had been transformed to have reduced toxicity of lipopolysaccharides, prepared in the same manner as in Example 2, were examined for ability to deliver not only drugs, but also drug-associated carriers of various sizes.

A mouse colon 26 cell line was subcutaneously injected at a dose of $1 \times 10^6$ cells into mice, and cultured for one week. PBS or a PBS solution containing 5 µg of shedding microvesicles derived from *E. coli* that had been transformed to have reduced toxicity of lipopolysaccharides was intravenously injected at a dose of 100 µl. After six hrs, 100 nm-sized green fluorescent beads were also intravenously injected, and allowed to sufficiently circulate through the body for 5 min. Thereafter, all the blood of the mice was substituted by PBS to remove fluorescent beads from blood vessels. Colon cancer tissues were excised, and cryosectioned at a thickness of 20 µm, followed by staining nuclei with 10 µg/ml of Hoechst dye. Fluorescent beads present within cancer tissues were observed under a confocal microscope. The results are given in FIG. 20.

Figure 20:
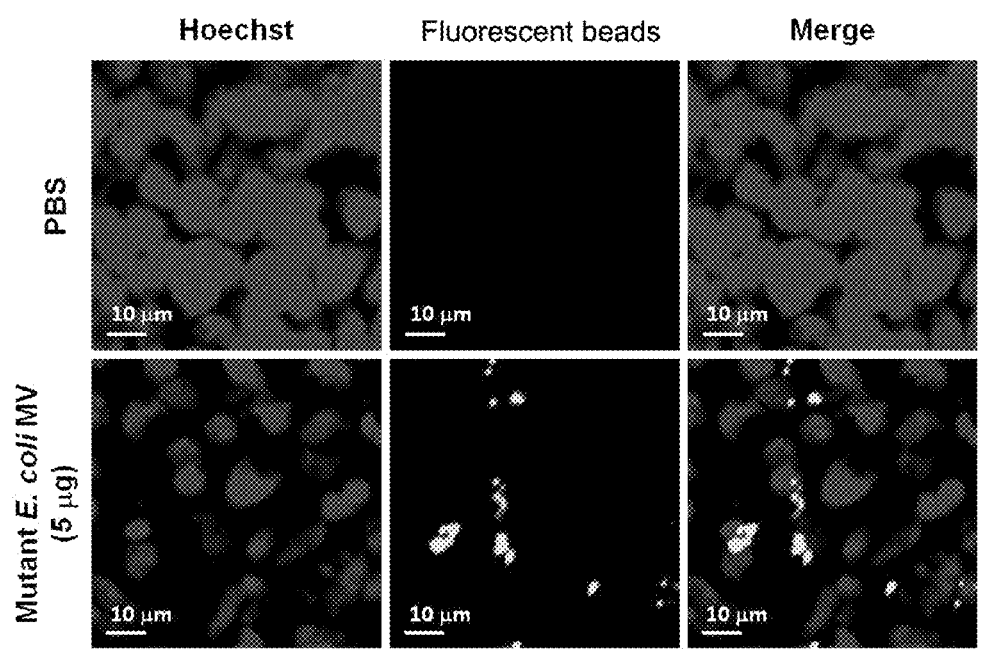
FIG. 20 shows images of cancer cells to which fluorescent beads with a size of 100 nm are delivered by shedding microvesicles derived from mutant *E. coli* transformed to have reduced toxicity of lipopolysaccharides (mutant *E. coli* MV), in animal models of colon cancer.

When the shedding microvesicles derived from *E. coli* that had been transformed to have reduced toxicity of lipopolysaccharides were injected, as shown in FIG. 20, 100-nm sized fluorescent beads were observed to exist within the cancer tissue. In contrast, PBS did not allowed the fluorescent beads to target the cancer tissue.

From these results, it can be inferred that the administration of bacterial cell-derived microvesicles leads to more effective delivery of a subsequently injected anticancer drug or anticancer drug-loaded carrier in a size of tens to hundreds nanometers to a cancer tissue.

Example 16

Anticancer Effect of OmpA, a Major Component of Bacterial Cell-Derived Microvesicles According to the proteomic analysis of the present inventors, OmpA, one of the most abundant outer membrane proteins of Gram-negative bacteria, was most abundantly found in shedding microvesicles. Thus, in order to examine whether OmpA functions to mediate the anticancer activity of bacterial cell-derived microvesicles, OmpA was assayed for anti-cancer activity.

A mouse colon 26 cell line was subcutaneously injected at a dose of $1 \times 10^6$ cells into mice, and cultured. After one week, PBS and a PBS solution containing 1 mg of a recombinant OmpA protein were injected at a dose of 100 µl twice a week via the tail vein into respective mouse groups of four. On day 21 after the transplantation of cancer cells, the sizes of colon cancer tissue were monitored. The volume of cancer tissue was calculated by the equation $V = l \times s^2 / 2$, wherein l is a length of the longest axis of a tumor and s is a length of the axis perpendicular to the longest axis. The measurement results are given in FIG. 21.

Figure 21:
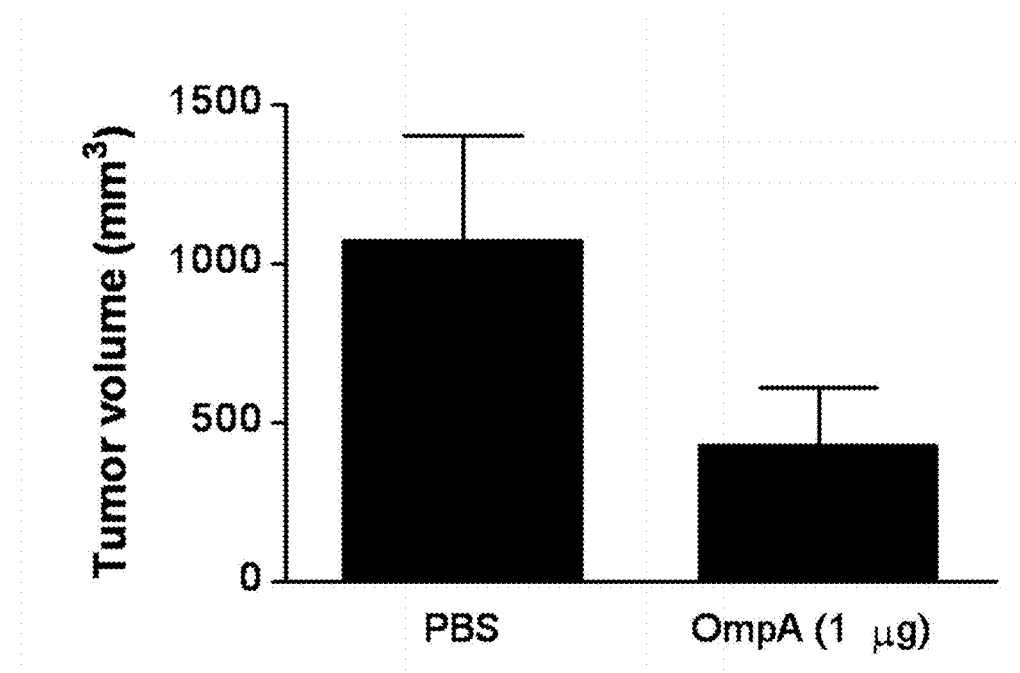
FIG. 21 is a graph showing the inhibition of OmpA, a major outer membrane protein of bacterial cell-derived shedding microvesicles against the growth of cancer tissues (tumor volume) in animal models of colon cancer.

As can be seen in FIG. 21, a significant reduction in the size of colon cancer tissues was obtained after the recombinant OmpA protein was administered, compared to the control. This result demonstrates that OmpA present in the outer membrane of bacterial cell-derived shedding microvesicles is a factor functioning to mediate the anticancer activity of bacterial cell-derived microvesicles.

Example 17

Anticancer Activity of Shedding Microvesicles Derived from Outer membrane Protein OmpF-Devoid Bacteria In addition to OmpA, the outer membrane protein OmpF was also found to be a major component of bacterial cell-derived shedding microvesicles according to the proteomic analysis result of the present inventors. Thus, OmpF-induced anticancer activity of bacterial cell-derived shedding microvesicles was assayed.

In this regard, shedding microvesicles were obtained in the same manner as in Example 2, with the exception that OmpF-devoid *E. coli* was employed.

A mouse colon 26 cell line was subcutaneously injected at a dose of $1\times10^6$ cells into mice, and cultured. After one week, PBS, a PBS solution containing 1 μg of wild-type *E. coli*-derived shedding microvesicles, and a PBS solution containing 1 μg of shedding microvesicles derived from OmpF-devoide *E. coli* were injected at a dose of 100 μl twice a week via the tail vein into respective mouse groups. On day 21 after the transplantation of cancer cells, the sizes of colon cancer tissue were monitored. The volume of cancer tissue was calculated by the equation $V=l\times s^2/2$, wherein l is a length of the longest axis of a tumor and s is a length of the axis perpendicular to the longest axis. The measurement results are given in FIG. 22.

Figure 22:
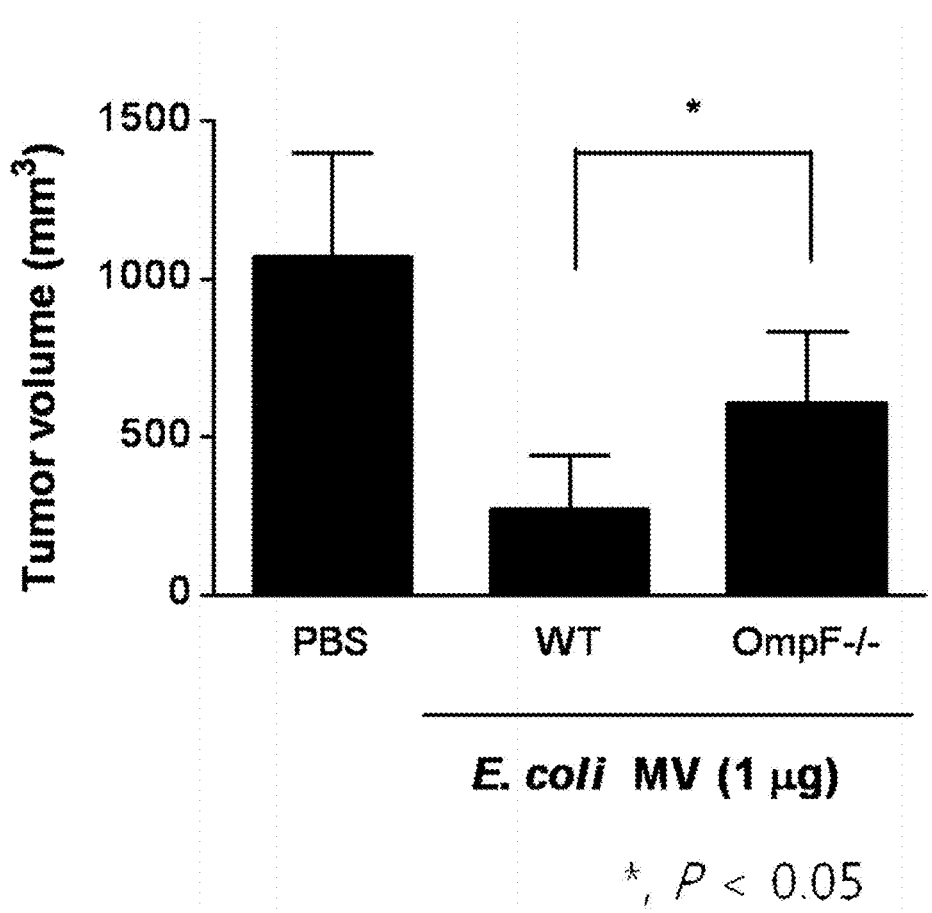
FIG. 22 is a graph showing the inhibition of shedding microvesicles (*E. coli* MV) derived from OmpF-knockout (OmpF$^{-/-}$) mutant *E. coli* and from the wild-type (WT) against the growth of cancer tissues (tumor volume) in animal models of colon cancer.

As can be seen in FIG. 22, the anticancer activity of the shedding microvesicles derived from OmpF-devoid *E. coli* was lower than that of the shedding microvesicles derived from wild-type *E. coli*.

This result demonstrates that together with OmpA, OmpF present in the outer membrane of bacterial cell-derived shedding microvesicles functions as a factor responsible for the anticancer activity of bacterial cell-derived microvesicles.

Example 18

Reconstitution of Liposome with OmpA Outer Membrane Protein

To construct liposomes, N-(carbonyl-methoxypolyethylene glycol 2000)-1,2-distearoyl-sn-glycero-3 phosphoethanolamine sodium salt (MPEG-DSPE), fully hydrogenated soy phosphatidylcholine (HSPC), and cholesterol were separately dissolved in a concentration of 3.19 mg/mL, 9.58 mg/mL, and 3.19 mg/mL, respectively, in chloroform, and the three lipid solutions were mixed at a ratio of 1:1:1. Then, chloroform was removed using nitrogen gas to form a thin film. Urea buffer (344 mM urea, 10 mM KCl, 10 mM HEPES (pH 7.0, 3 mM $NaN_3$) was added to this thin film, followed by ultrasonication at 56° C. for 1 hr in a water bath sonicator. The resulting suspension was forced to pass five times through a membrane filter with a pore size of 1 μm, then five times through a membrane filter with a pore size of 400 nm, and finally five times through a membrane filter with a pore size of 100 nm to afford liposomes.

To 0.3 ml of the liposomes was added 0.7 ml of urea buffer containing 280 μg of OmpA, followed by octyl-β-D-glucopyranoside to the final concentration of 1.1%. After incubation at 37° C. for 2 hrs, 15 ml of urea buffer was added. The resulting solution was ultracentrifuged at 100,000×g for 1 hr. The pellet was suspended in 0.2 ml of urea buffer, and added to 50% OptiPrep solution to form a final concentration of 30%. In a 5 ml ultracentrifuge tube, 2 ml of the 30% liposome suspension, 1 ml of 20% OptiPrep, and 1 ml of 5% OptiPrep were placed in that order. Ultracentrifugation at 100,000×g for 2 hrs formed an OmpA-loaded liposome layer between the 20% OptiPrep layer and the 5% OptiPrep layer.

After 200 ng of OmpA and 5 μg of the OmpA-loaded liposomes were separately mixed with 5× loading dye, the mixtures were boiled at 100° C. for 5 min, and loaded to 12% polyacrylamide gel. Electrophoresis was performed at 80 V for 2 hrs, after which proteins were transferred onto a PVDF membrane at 400 mA for 2 hrs. The membrane was blocked at room temperature in 3% skim milk in PBS, incubated with an OmpA antibody at 4° C. for 12 hrs, and washed twice with PBS. Following incubation with a peroxidase-conjugated secondary antibody at room temperature for 1 hr, the membrane was washed for 30 min in PBS, and subjected to color development with an ECL substrate. The result is given in FIG. 23.

Figure 23:
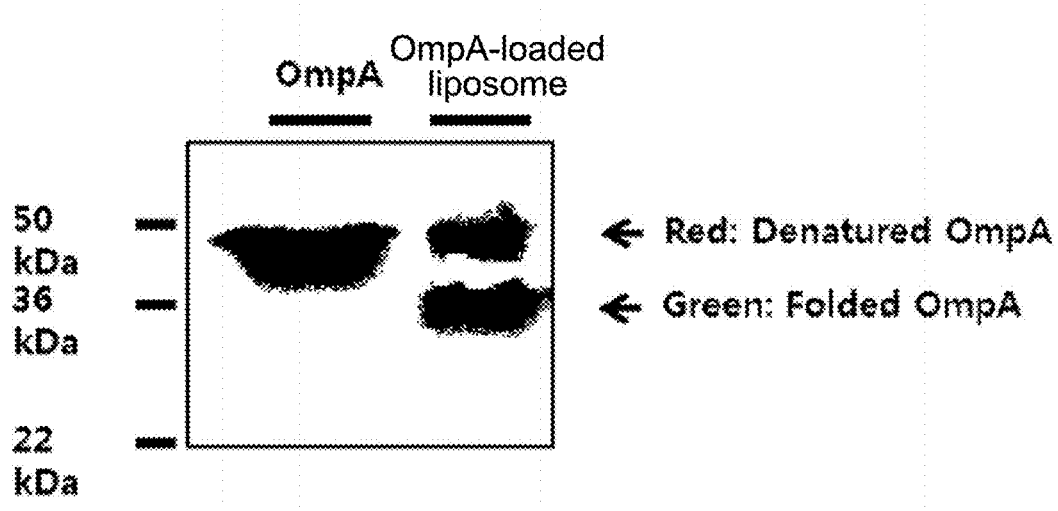
FIG. 23 is a view showing the presence of OmpA in liposomes after OmpA, a component of bacterial cell-derived microvesicles, was reconstituted to liposomes serving as a nanoparticle carrier.

As can be seen in FIG. 23, OmpA was found to be loaded to liposomes. The OmpA protein, when isolated, is in a denatured form because it exists together with a detergent. However, when reconstituted into liposomes, OmpA is found to exist as both folded and denatured forms. From the result, it is understood that OmpA can be reconstituted into liposomes.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described hitherto, the bacterial cell-derived microvesicles of the present invention can specifically deliver substances therapeutic or diagnostic for various diseases including cancer to cells or tissues of interest, thereby increasing therapeutic and diagnostic efficacy.

Moreover, the bacterial cell-derived microvesicles with therapeutic and/or diagnostic substances loaded thereto and the preparation method thereof in accordance with the present invention may be used for in vitro and/or in vivo treatment, diagnosis or experiments.

The invention claimed is:

1. A method of treating cancer in a subject in need thereof, said method comprising administering bacterial cell-derived microvesicles to said subject,
   wherein the bacterial cell-derived microvesicles are derived from a Gram-positive bacteria that is genetically transformed to have a reduced toxicity; and
   wherein the cancer is treated.

2. The method of claim 1, wherein the bacteria express a substance that is therapeutic for cancer or are transformed to express the substance that is therapeutic for cancer.

3. The method of claim 1, wherein the bacteria are transformed so that the microvesicles are mitigated in toxicity.

4. The method of claim 1, wherein the microvesicles are loaded with a drug which mitigates the side effects of the microvesicles or a drug which enhances the anticancer activity of the microvesicles.

5. The method of claim 4, wherein the drug which mitigates the side effects of the microvesicles is aspirin.

6. The method of claim 4, wherein the drug enhancing anticancer activity of the microvesicles is selected from the group consisting of a drug suppressing Th17(T helper 17 cell)-mediated immune responses, a drug suppressing formation or activity of interleukin-6, a drug suppressing angiogenesis, a drug suppressing formation or activity of vascular endothelial growth factor, a drug suppressing vascular endothelial growth factor receptor-mediated signaling, a drug suppressing STAT3 (Signal transducer and activator of transcription) signaling, and an anticancer agent.

7. The method of claim 1, wherein the genetically transformed bacteria is a LTA mutant.

8. The method of claim 1, wherein the genetically transformed bacteria comprises a mutation in the LTA gene, wherein the mutated LTA is less immunogenic than the wild-type.

\* \* \* \* \*